(12) United States Patent
Kagan et al.

(10) Patent No.: US 7,220,284 B2
(45) Date of Patent: May 22, 2007

(54) GASTROINTESTINAL SLEEVE DEVICE AND METHODS FOR TREATMENT OF MORBID OBESITY

(75) Inventors: Jonathan Kagan, Hopkins, MN (US); James Balliro, Jackson, WY (US); Mitchell Dann, Wilson, WY (US); Lee Guterman, Amherst, NY (US)

(73) Assignee: ValenTx, Inc., Carpinteria, CA (US)

( * ) Notice: Subject to any disclaimer, the term of this patent is extended or adjusted under 35 U.S.C. 154(b) by 106 days.

(21) Appl. No.: 11/169,341

(22) Filed: Jun. 29, 2005

(65) Prior Publication Data

US 2005/0240279 A1    Oct. 27, 2005

Related U.S. Application Data

(63) Continuation of application No. 10/699,589, filed on Oct. 31, 2003, now Pat. No. 7,037,344.

(60) Provisional application No. 60/442,987, filed on Nov. 1, 2002.

(51) Int. Cl.
*A61F 2/04* (2006.01)
(52) U.S. Cl. .................... 623/23.65; 606/153; 606/139
(58) Field of Classification Search .. 623/23.65–23.68; 606/139, 153
See application file for complete search history.

(56) References Cited

U.S. PATENT DOCUMENTS

| 4,006,747 A | 2/1977 | Kronenthal et al. |
|---|---|---|
| 4,134,405 A | 1/1979 | Smit |
| 4,235,238 A | 11/1980 | Ogiu et al. |
| 4,315,509 A | 2/1982 | Smit |
| 4,501,264 A | 2/1985 | Rockey |
| 4,532,926 A | 8/1985 | O'Holla |
| 4,641,653 A | 2/1987 | Rockey |
| 4,763,653 A | 8/1988 | Rockey |
| 4,846,836 A | 7/1989 | Reich |
| RE34,021 E | 8/1992 | Mueller et al. |
| 5,236,423 A | 8/1993 | Mix et al. |
| 5,306,300 A | 4/1994 | Berry |

(Continued)

FOREIGN PATENT DOCUMENTS

EP    0817598    2/1996

(Continued)

OTHER PUBLICATIONS

*Endoscopic suturing*, C. Paul Swain MD, *Balliere's Clinical Gastroenterology*, vol. 13, No. 1. pp. 97-108, 1999.

(Continued)

*Primary Examiner*—Suzette Gherbi
(74) *Attorney, Agent, or Firm*—Knobbe, Martens, Olson & Bear, LLP

(57) ABSTRACT

Apparatus and methods are described for treatment of morbid obesity using minimally invasive techniques. The apparatus includes a system of components that may be used separately or in combination for effectively reducing stomach volume, bypassing a portion of the stomach and/or small intestines, reducing nutrient absorption in the stomach and/or small intestines and/or depositing minimally or undigested food farther than normal into the intestines, thereby stimulating intestinal responses. The components described include an artificial stoma device, a gastric sleeve device, an intestinal sleeve device and a combined gastrointestinal sleeve device.

67 Claims, 14 Drawing Sheets

U.S. PATENT DOCUMENTS

| | | | |
|---|---|---|---|
| 5,314,473 A | 5/1994 | Godin | |
| 5,470,337 A | 11/1995 | Moss | |
| 5,820,584 A | 10/1998 | Crabb | |
| 5,843,164 A | 12/1998 | Frantzen et al. | |
| 5,861,036 A | 1/1999 | Godin | |
| 5,887,594 A | 3/1999 | LoCicero, III | |
| 5,957,940 A | 9/1999 | Tanner et al. | |
| 5,972,023 A | 10/1999 | Tanner et al. | |
| 6,113,609 A | 9/2000 | Adams | |
| 6,254,642 B1 | 7/2001 | Taylor | |
| 6,264,700 B1 | 7/2001 | Kilcoyne et al. | |
| 6,387,104 B1 | 5/2002 | Pugsley, Jr. et al. | |
| 6,409,656 B1 | 6/2002 | Sangouard et al. | |
| 6,494,888 B1 | 12/2002 | Laufer et al. | |
| 6,535,764 B2 | 3/2003 | Imran et al. | |
| 6,544,291 B2 | 4/2003 | Taylor | |
| 6,558,400 B2 | 5/2003 | Deem et al. | |
| 6,558,429 B2 | 5/2003 | Taylor | |
| 6,593,596 B1 | 7/2003 | Geitz | |
| 6,626,919 B1 | 9/2003 | Swanstorm | |
| 6,675,809 B2 | 1/2004 | Stack et al. | |
| 6,699,263 B2 | 3/2004 | Cope | |
| 6,702,735 B2 | 3/2004 | Kelly | |
| 6,736,828 B1 | 5/2004 | Adams et al. | |
| 6,740,121 B2 | 5/2004 | Geitz | |
| 6,746,489 B2 | 6/2004 | Dua et al. | |
| 6,764,518 B2 | 7/2004 | Godin | |
| 6,790,237 B2 | 9/2004 | Stinson | |
| 6,845,776 B2 | 1/2005 | Stack et al. | |
| 2001/0016748 A1 | 8/2001 | Tanner et al. | |
| 2001/0044595 A1 | 11/2001 | Reydel et al. | |
| 2002/0016607 A1 | 2/2002 | Bonadio et al. | |
| 2002/0082621 A1 | 6/2002 | Schurr et al. | |
| 2002/0165589 A1 | 11/2002 | Imaran et al. | |
| 2002/0183768 A1 | 12/2002 | Deem et al. | |
| 2003/0093117 A1 | 5/2003 | Saadat | |
| 2003/0109931 A1 | 6/2003 | Geitz | |
| 2003/0130560 A1 | 7/2003 | Suzuki et al. | |
| 2003/0191497 A1 | 10/2003 | Cope | |
| 2003/0199989 A1 | 10/2003 | Stack et al. | |
| 2004/0006351 A1* | 1/2004 | Gannoe et al. | 606/139 |
| 2004/0039452 A1* | 2/2004 | Bessler | 623/23.65 |
| 2004/0044364 A1 | 3/2004 | DeVries et al. | |
| 2004/0082963 A1* | 4/2004 | Gannoe et al. | 606/153 |
| 2004/0087976 A1 | 5/2004 | DeVries et al. | |
| 2004/0092892 A1 | 5/2004 | Kagan et al. | |
| 2004/0092974 A1 | 5/2004 | Gannoe et al. | |
| 2004/0097986 A1 | 5/2004 | Adams | |
| 2004/0102855 A1 | 5/2004 | Shank | |
| 2004/0107004 A1 | 6/2004 | Levine et al. | |
| 2004/0117031 A1 | 6/2004 | Stack et al. | |
| 2004/0122456 A1 | 6/2004 | Saadat et al. | |
| 2004/0122473 A1 | 6/2004 | Ewers et al. | |
| 2004/0133147 A1 | 7/2004 | Woo | |
| 2004/0133238 A1 | 7/2004 | Cerier | |
| 2004/0138525 A1 | 7/2004 | Saadat et al. | |
| 2004/0143342 A1 | 7/2004 | Stack et al. | |
| 2004/0148034 A1 | 7/2004 | Kagan et al. | |
| 2004/0153167 A1 | 8/2004 | Stack et al. | |
| 2004/0158331 A1 | 8/2004 | Stack et al. | |
| 2004/0167546 A1 | 8/2004 | Saadat et al. | |
| 2004/0186514 A1 | 9/2004 | Swain et al. | |
| 2004/0220682 A1 | 11/2004 | Levine et al. | |
| 2004/0243152 A1 | 12/2004 | Taylor et al. | |
| 2004/0249362 A1 | 12/2004 | Levine et al. | |
| 2005/0033331 A1 | 2/2005 | Burnett et al. | |
| 2005/0033332 A1 | 2/2005 | Burnett | |
| 2005/0075654 A1 | 4/2005 | Kelleher | |
| 2005/0080444 A1 | 4/2005 | Kraemer et al. | |
| 2005/0085787 A1 | 4/2005 | Laufer | |
| 2005/0085923 A1 | 4/2005 | Levine et al. | |
| 2005/0096673 A1 | 5/2005 | Stack et al. | |
| 2005/0125020 A1 | 6/2005 | Meade et al. | |
| 2005/0125075 A1 | 6/2005 | Meade et al. | |
| 2005/0143784 A1 | 6/2005 | Imran | |
| 2005/0187567 A1 | 8/2005 | Baker et al. | |
| 2005/0192629 A1 | 9/2005 | Jaadat et al. | |
| 2005/0197714 A1 | 9/2005 | Sayet | |
| 2005/0197715 A1 | 9/2005 | Kugler et al. | |
| 2005/0203547 A1 | 9/2005 | Weller et al. | |
| 2005/0247320 A1 | 11/2005 | Stack et al. | |
| 2005/0261549 A1 | 11/2005 | Hewit et al. | |
| 2005/0261712 A1 | 11/2005 | Balbierz et al. | |
| 2005/0267499 A1 | 12/2005 | Stack et al. | |
| 2006/0009858 A1 | 1/2006 | Levine et al. | |
| 2006/0020164 A1 | 1/2006 | Butler et al. | |
| 2006/0020277 A1 | 1/2006 | Gostout et al. | |
| 2006/0020278 A1 | 1/2006 | Burnett et al. | |
| 2006/0025819 A1 | 2/2006 | Nobis et al. | |
| 2006/0047289 A1 | 3/2006 | Fogel | |
| 2006/0064120 A1 | 3/2006 | Levine et al. | |
| 2006/0155312 A1 | 7/2006 | Levine et al. | |
| 2006/0161139 A1 | 7/2006 | Levine et al. | |
| 2006/0161172 A1 | 7/2006 | Levine et al. | |
| 2006/0161187 A1 | 7/2006 | Levine et al. | |
| 2006/0161265 A1 | 7/2006 | Levine et al. | |

FOREIGN PATENT DOCUMENTS

| | | | |
|---|---|---|---|
| EP | 1237501 | 9/2000 | |
| WO | WO 80/00007 | * 1/1980 | 623/23.65 |
| WO | WO 91/01117 | 2/1991 | |
| WO | WO 96/29954 | 10/1996 | |
| WO | WO 00/12027 | 3/2000 | |
| WO | WO 01/43863 | 6/2001 | |
| WO | WO 03/017882 A2 | 3/2003 | |
| WO | WO 03/086247 A1 | 10/2003 | |
| WO | WO 03/094785 A1 | 11/2003 | |
| WO | WO 2004/017863 A2 | 3/2004 | |
| WO | WO 2004/047686 | 6/2004 | |
| WO | WO 2004/049982 A2 | 6/2004 | |
| WO | WO 2004/064680 A1 | 8/2004 | |
| WO | WO 2004/080336 A2 | 9/2004 | |
| WO | WO 2004/086984 A1 | 11/2004 | |
| WO | WO 2004/103214 A1 | 12/2004 | |
| WO | WO 2004/105643 | 12/2004 | |
| WO | WO 2005/011519 | 2/2005 | |
| WO | WO 2005/032422 | 4/2005 | |
| WO | WO 2005/037152 A1 | 4/2005 | |
| WO | WO 2005/060869 A1 | 7/2005 | |
| WO | WO 2005/060882 A1 | 7/2005 | |
| WO | WO 2006/044640 A1 | 4/2006 | |

OTHER PUBLICATIONS

*Endoscopic Suturing of a Novel Gastroesophageal Antireflux Device (GARD) A Prelinary Report*, N.J. Godin et al., Gastrointestinal Endoscopy, vol. 43, No. 4, 1996.

*An endoscopic stapling device: the development of new flexible endoscopically controlled device for placing multiple transmural staples in gastrointestinal tissue*, C. Paul Swain, MD et al., Gastrointestinal Endoscopy, vol. 35, No. 4, 1989 pp. 338-339.

*An endoscopically deliverable tissue-transfixing device for securing biosensors in the gastrointestinal tract*, C. Paul Swain, MD et al. Gastrointestinal Endoscopy, 1994 vol. 40 No. 6 pp. 730-734.

*Development of a gastroplasty with variable diameter. Experimental study using artificial sphincters*, M. Merlini et al., 1992 Abstract.

*A through-the-scope device of suturing and tissue approximation under EUS control*, Annette Fritscher-Ravens, MD, et al., *Gastrointestinal Endoscopy*, vol. 56, No. 5, 2002, pp. 737-742.

*Bard EndoCinch: the device, the technique and pre-clinical studies*, Paul Swain, M.D. et al., *Gastrointestinal Endoscopy Clinics of North America*, 13, 2003 pp. 75-88.

*Microvasive gastric stapler: the device, technique, and preclinical results*, Tom R. De Meester MD, *Gastrointestinal Endoscopy Clinics of North America*, 13 (2003) pp. 117-133.

*Transgastric gastropexy and hiatal hernia repair for GERD under EUS control: a porcine model*, Annette Fritscher-Ravens, MD et al., *Gastrointestinal Endoscopy*, vol. 59, No. 1, 2004, pp. 89-95.

*T=Anchor Introducer Gun™ Details*, Moss™ Tubes Brochure.

Sew-Right® SR 5™ & SR 10™, Ti-KNOT® TK 5™ Advertisement received at ASBS Conference 2002.

* cited by examiner

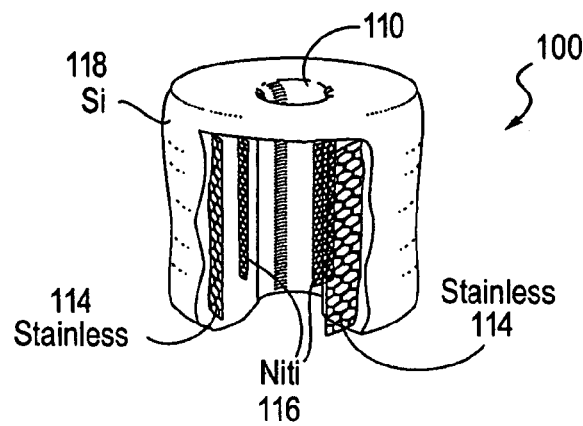
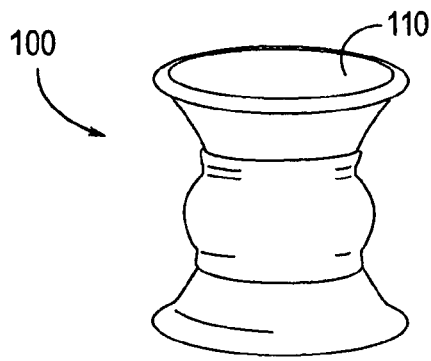
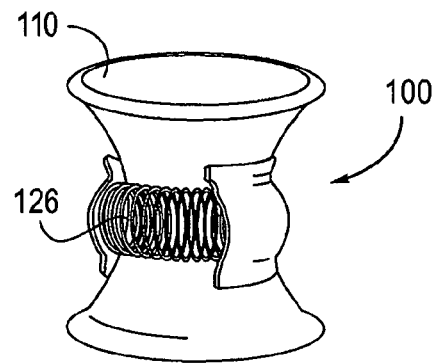
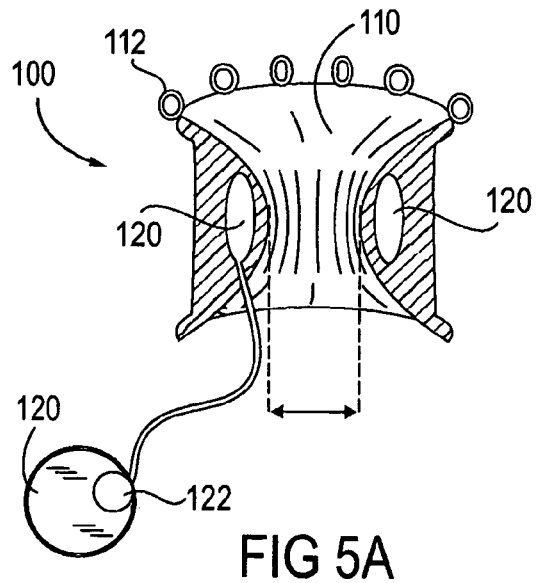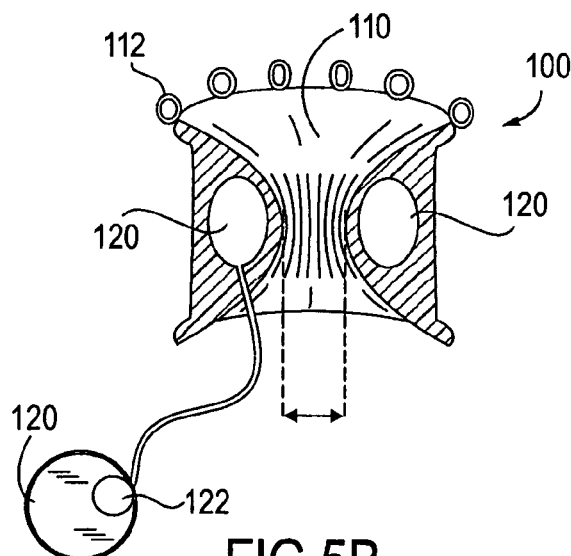

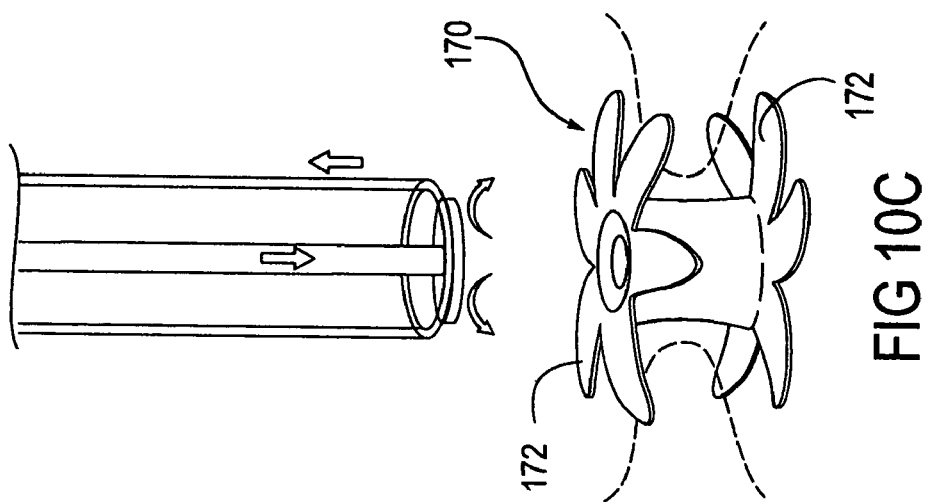
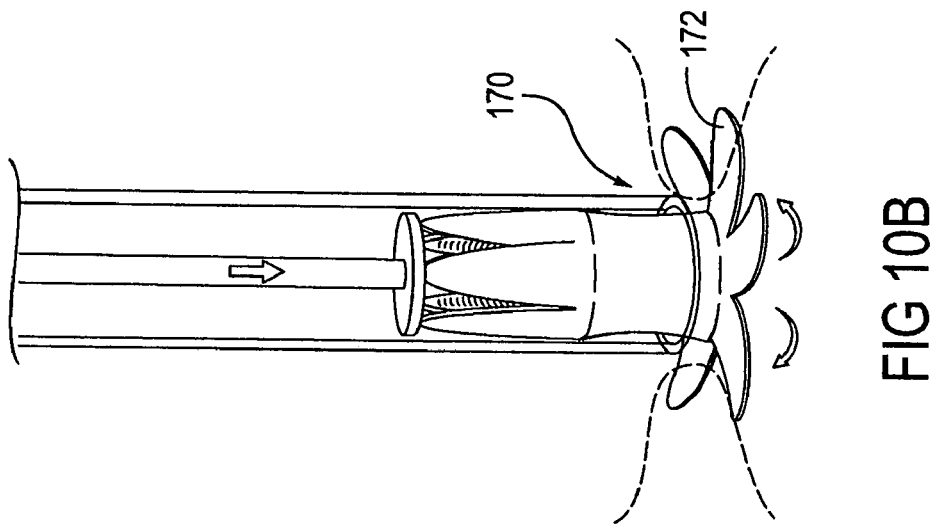
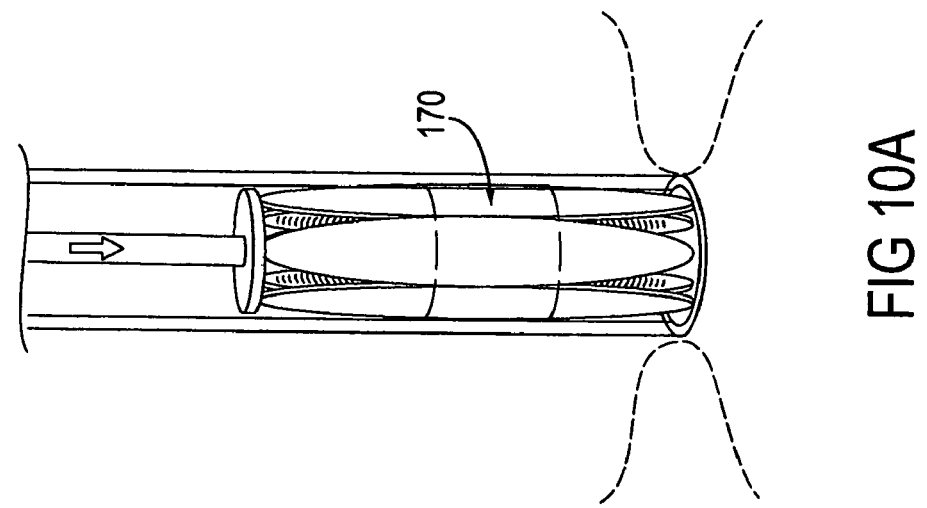

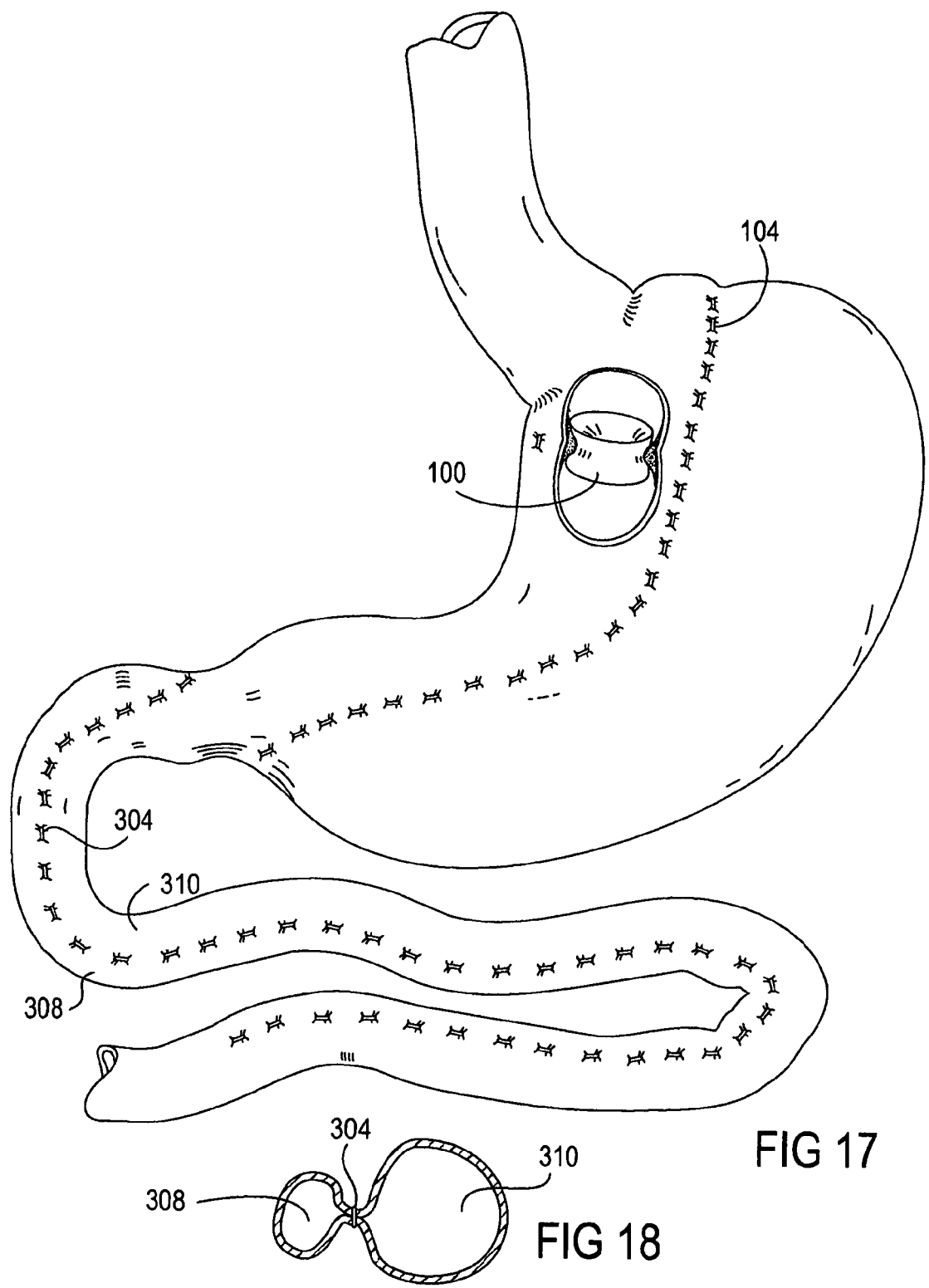

GASTROINTESTINAL SLEEVE DEVICE AND METHODS FOR TREATMENT OF MORBID OBESITY

CROSS-REFERENCE TO RELATED APPLICATIONS

The present application is a continuation of U.S. patent application Ser. No. 10/699,589, filed on Oct. 31, 2003 now U.S. Pat. No.7,037,344, for Apparatus and Methods for Treatment of Morbid Obesity, which claims priority of U.S. Provisional Patent Application 60/442,987, filed on Nov. 1, 2002, for Apparatus and Methods for Treatment of Morbid Obesity. This and all other patents and patent applications referred to herein are hereby incorporated by reference in their entirety.

FIELD OF THE INVENTION

The present invention relates generally to apparatus and methods for treatment of morbid obesity. In particular, it relates to apparatus and methods that can be applied using minimally invasive techniques for effectively reducing stomach volume, bypassing a portion of the stomach and/or small intestines and reducing nutrient absorption in the stomach and/or small intestines.

BACKGROUND OF THE INVENTION

Bariatrics is the field of medicine encompassing the study of overweight, its causes, prevention and treatment. Bariatric surgery is a treatment for morbid obesity that involves alteration of a patient's digestive tract to encourage weight loss and to help maintain normal weight. The following history of bariatric surgery is provided by the American Society for Bariatric Surgery.

JEJUNO-ILEAL BYPASS: Kremen and Linner's Jejuno-ileal Bypass: Bariatric surgery has continually evolved since its initial sporadic and tentative introduction in the 1950's. The first bariatric procedure to be preceded by animal studies and subsequently presented to a recognized surgical society and published in a peer-reviewed journal was that of Kremen and associates in 1954. (Kremen, Linner et al. 1954) The case, which they presented, was of a jejuno-ileal bypass (JIB). Jejuno-ileal bypass involved joining the upper small intestine to the lower part of the small intestine, bypassing a large segment of the small bowel, which is thus taken out of the nutrient absorptive circuit. In the discussion of the case, Philip Sandblom of Lund, Sweden, alluded to the fact that, two years previously, Victor Henriksson of Gothenberg, Sweden, had performed a similar procedure for morbid obesity. In this case the redundant small bowel was excised rather than bypassed. Subsequently it was discovered that Dr. Richard Varco of the University of Minnesota independently performed JIB at the University of Minnesota Hospitals around the same time as the operation of Kremen et al. Varco's case was unpublished and the patient record lost, so that the exact procedure date is unknown. (Buchwald and Rucker 1984)

JEJUNO-COLIC BYPASS: As part of an ongoing study of morbid obesity, Payne et al. reported results of ten patients in whom an end-to-side jejuno-colic shunt had been performed. (Payne, DeWind et al. 1963) In jejuno-colic shunt, the upper small bowel was joined even further down the intestinal tract, to the colon, with the idea of bypassing an even longer segment of the nutrient absorptive gastrointestinal tract. These patients had episodes of uncontrollable diarrhea, dehydration and electrolyte imbalance. Because of the problem with diarrhea, most of these surgeries were eventually taken down and converted to end-to-side jejuno-ileostomies. Payne and Dewind subsequently advised against jejunocolic anastomoses, instead recommending end-to-side jejuno-ileostomy anastomosing the first 14 inches of jejunum to the last 4 inches of ileum. (Payne and DeWind 1969)

PROBLEMS WITH JEJUNO-ILEAL BYPASS: (JIB) Two variants of jejunoileal anastomosis were developed, the end-to-side (Payne and DeWind 1969) and end-to end (Scott, Dean et al. 1973) anastomoses of the proximal jejunum to distal ileum. In both instances an extensive length of small intestine was bypassed, not excised, excluding it from the alimentary stream.

In both these variants a total of only about 35 cm (18") of normally absorptive small intestine was retained in the absorptive stream, compared with the normal length of approximately 7 meters (twenty feet). In consequence, malabsorption of carbohydrate, protein, lipids, minerals and vitamins inevitably occur, Where the end-to-side technique was used, reflux of bowel content back up the defunctionalized small intestine allowed absorption of some of the refluxed material resulting in less weight loss initially and greater subsequent weight regain.

Bile is secreted by the liver, enters the upper small intestine by way of the bile duct, and is absorbed in the small intestine. Bile has an important role in fat digestion, emulsifying fat as the first stage in its digestion. Bypassing the major site of bile acid reabsorption in the small intestine therefore further reduces fat and fat soluble vitamin absorption. As a result, huge amounts of fatty acids, which are normally absorbed in the small intestine, enter the colon where they cause irritation of the colon wall and the secretion of excessive volumes of water and electrolytes, especially sodium and potassium, leading to diarrhea. This diarrhea is the major patient complaint and has characterized jejunoileal bypass in the minds of patient and physician alike since the procedure was introduced.

Bile salts help to keep cholesterol in solution in the bile. Following JIB, the bile salt pool is decreased as a consequence of reduced absorption in the small intestine and bile salt losses in the stool. The relative cholesterol concentration in gallbladder bile rises and cholesterol crystals precipitate in the gallbladder bile, forming a nidus for development of cholesterol gallstones in the gallbladder. Specific vitamin deficiencies also occur; Vitamin D and Calcium deficiencies lead to thinning of bone with bone pain and fractures as a result of osteoporosis and osteomalacia. Bypass of the terminal ileum, which is the specific site of Vitamin B12 absorption, leads to Vitamin B12 deficiency with a specific peripheral neuropathy. Vitamin A deficiency can induce night blindness. Calcium Oxalate renal stones occur commonly following JIB, along with increased colonic absorption of oxalate. The colonic absorption of oxalate has been attributed to:

1. Exposure of colonic mucosa to excessive bile salts and possibly bile acids, increasing colonic permeability to oxalate, or 2. Excessive quantities of fatty acids in the gut form soaps with calcium, reducing its availability to form insoluble calcium oxalate leading to the persistence of soluble and absorbable oxalate in the colon.

Patients with intestinal bypass develop diarrhea 4-6 times daily. The frequency of stooling varying directly with fat intake. There is a general tendency for stooling to diminish with time, as the short segment of small intestine remaining in the alimentary stream increases in size and thickness, developing its capacity to absorb calories and nutrients, thus producing improvement in the patients nutrition and counterbalancing the ongoing weight loss. This happy result does not occur in every patient, but approximately one third of those undergoing "Intestinal Bypass" have a relatively benign course. Unfortunately, even this group is at risk of significant late complications, many patients developing irreversible hepatic cirrhosis several years after the procedure.

JIB is the classic example of a malabsorptive weight loss procedure. Some modern procedures utilize a lesser degree of malabsorption combined with gastric restriction to induce and maintain weight loss. Any procedure involving malabsorption must be considered at risk to develop at least some of the malabsorptive complications exemplified by JIB. The multiple complications associated with JIB while considerably less severe than those associated with Jejunocolic anastomosis, were sufficiently distressing both to the patient and to the medical attendant to cause the procedure to fall into disrepute.

Listing of jejuno-ileal bypass complications:
Mineral and Electrolyte Imbalance:
Decreased serum sodium, potassium, magnesium and bicarbonate
Decreased sodium chloride
Osteoporosis and osteomalacia secondary to protein depletion, calcium and vitamin D loss, and acidosis
Protein Calorie Malnutrition:
Hair loss, anemia, edema, and vitamin depletion
Cholelithiasis
Enteric Complications:
Abdominal distension, irregular diarrhea, increased flatus, pneumatosis intestinalis, colonic pseudo-obstruction, bypass enteropathy, volvulus with mechanical small bowel obstruction
Extra-intestinal Manifestations:
Arthritis
Liver disease, occurs in at least 30%
Acute liver failure may occur in the postoperative period, and may lead to death acutely following surgery.
Steatosis, "alcoholic" type hepatitis, cirrhosis, occurs in 5%, progresses to cirrhosis and death in 1-2%
Erythema Nodosum, non-specific pustular dermatosis
Weber-Christian Syndrome
Renal Disease:
Hyperoxaluria, with oxalate stones or interstitial oxalate deposits, immune complex nephritis, "functional" renal failure.
Miscellaneous:
Peripheral neuropathy, pericarditis, pleuritis, hemolytic anemia, neutropenia, and thrombocytopenia The multiple complications associated with JIB led to a search for alternative procedures, one of which was gastric bypass, a procedure that is described in detail later. In 1983 Griffen et al. reported a comprehensive series comparing the results of jejuno-ileal bypass with gastric bypass. 11 of 50 patients who underwent JIB required conversion to gastric bypass within 5 years, leading Griffen to abandon jejuno-ileal bypass. (Griffen, Bivins et al. 1983)

JIB can be summed up as having:
a. Good Weight Loss,
b. Malabsorption with multiple deficiencies,
c. Diarrhea.

As a consequence of all these complications, jejuno-ileal bypass is no longer a recommended Bariatric Surgical Procedure. Indeed, the current recommendation for anyone who has undergone JIB, and still has the operation intact, is to strongly consider having it taken down and converted to one of the gastric restrictive procedures.

BILIOPANCREATIC DIVERSION: A modern variant of the Jejuno-ileal Bypass (JIB) is Biliopancreatic Diversion (BPD), a procedure that differs from JIB in that no small intestine is defunctionalized and, consequently, liver problems are much less frequent. This procedure was developed by Professor Nicola Scopinaro, of the University of Genoa, Italy. (Scopinaro, Gianetta et al. 1996)

This procedure has two components. A limited gastrectomy results in reduction of oral intake, inducing weight loss, especially during the first postoperative year. The second component of the operation, construction of a long limb Roux-en-Y anastomosis with a short common "alimentary" channel of 50 cm length. This creates a significant malabsorptive component that acts to maintain weight loss long term. Dr. Scopinaro recently published long-term results of this operation, reporting 72% excess body weight loss maintained for 18 years. These are the best results, in terms of weight loss and duration of weight loss, reported in the bariatric surgical literature to this date.

From the patient's perspective, the great advantages of this operation are the ability to eat large quantities of food and still achieve excellent, long-term weight loss results. Disadvantages of the procedure are the association with loose stools, stomal ulcers, and foul smelling stools and flatus. The most serious potential complication is protein malnutrition, which is associated with hypoalbuminemia, anemia, edema, asthenia, alopecia, generally requires hospitalization and 2-3 weeks hyperalimentation. BPD patients need to take supplemental calcium and vitamins, particularly Vitamin D, lifelong. Because of this potential for significant complications, BPD patients require lifelong follow-up. In BPD patients who have received 200-300 cm alimentary limbs because of protein malnutrition concerns, the incidence of protein malnutrition fell dramatically to range from 0.8% to 2.3%.

In 1988, Hess, using a combination of Scopinaro's BPD and the duodenal switch described by DeMeester in 1987, developed a hybrid operation with the advantages of the BPD, but without some of the associated problems. The duodenal switch, originally designed for patients with bile reflux gastritis, consists of a suprapapillary Roux-en-Y duodeno-jejunostomy. This allows the first portion of the duodenum to remain in the alimentary stream thus reducing the incidence of stomal ulcer. When combined with a 70%-80% greater curvature gastrectomy (sleeve resection of the stomach) continuity of the gastric lesser curve is maintained while simultaneously reducing stomach volume. A long limb Roux-en-Y is then created. The efferent limb acts to decrease overall caloric absorption and the long biliopancreatic limb diverting bile from the alimentary contents, specifically to induce fat malabsorption. This technique, was first presented by Hess in 1992 and first published in a paper by Marceau, Biron et al. in 1993 is known as Biliopancreatic Diversion with Duodenal Switch (BPDDS). This procedure is claimed to essentially eliminate stomal ulcer and dumping syndrome.

BPD and its variants are the most major procedures performed for obesity and it follows that prospective patients who wish to consider BPD should seek out experienced surgeons with life-long follow up programs.

Listing of complications of biliopancreatic diversion:
Protein Malnutrition 15%
Incisional hernia 10%
Intestinal obstruction 1%

Acute biliopancreatic limb obstruction Stomal Ulcer 3.0%

Bone Demineralization: Pre-op 25%; at 1-2 yrs, 29%; at 3-5 yrs 53%; at 6-10 yrs 14%.

Hemorrhoids 4.3%

Acne 3.5%

Night Blindness 3%

Operative Mortality 0.4%-0.8% (1122 subjects, 1984-1993)

GASTRIC BYPASS: Gastric Bypass (RGB) was developed by Dr. Edward E. Mason, of the University of Iowa, based on the observation that females who had undergone partial gastrectomy for peptic ulcer disease, tended to remain underweight following the surgery, and that it was very difficult to achieve weight gain in this patient group. He therefore applied the principles of partial gastrectomy to obese females, finding that they did indeed lose weight. (Mason and Ito 1967) With the availability of surgical staples, he was able to create a partition across the upper stomach using staples, and did not require removal of any of the stomach. Subsequent modifications of the technique include a pouch of 50 ml or less, a gastroenterostomy stoma of 0.9 mm, use of the Roux-en-Y technique to avoid loop gastroenterostomy and the bile reflux that may ensue. Lengthening of the Roux limb to 100-150 cm to include a greater element of malabsorption and improve weight loss and the use of the retrocolic and retrogastric routing of the gastrojejunostomy to ease the technical difficulties of the procedure and improve long term weight loss results. Staple line failures have been found to occur many years after the procedure, in consequence surgeons have responded by use of techniques designed to prevent this. These include transection of the stomach, in which the staple line is divided and the cut ends oversewn. An alternative technique using superimposed staple rows is claimed to exert its effect by crushing the stomach tissue causing firm scarring along the staple line. Additionally, there have been attempts to stabilize the gastroenterostomy by the use of a prosthetic band, fashioned into a ring positioned just above the junction of gastric pouch and small intestine. Gastric Bypass has also stood the test of time, with one series of greater than 500 cases, followed for 14 years, maintaining 50% excess weight loss.

The complications of gastric bypass are much less severe than those of Intestinal Bypass, and most large series report complications in two phases, those that occur shortly after surgery, and those that take a longer time to develop. The most serious acute complications include leaks at the junction of stomach and small intestine. This dangerous complication usually requires that the patient be returned to surgery on an urgent basis, as does the rare acute gastric dilatation, which may arise spontaneously or secondary to a blockage occurring at the Y-shaped anastomosis (jejunojejunostomy). Then there are the complications to which any obese patient having surgery is prone, these including degrees of lung collapse (atelectasis), which occur because it is hard for the patient to breathe deeply when in pain. In consequence a great deal of attention is paid in the postoperative period to encouraging deep breathing and patient activity to try to minimize the problem. Blood clots affecting the legs are more common in overweight patients and carry the risk of breaking off and being carried to the lungs as a pulmonary embolus. This is the reason obese patients are usually anticoagulated before surgery with a low dose of Heparin or other anticoagulant. Wound infections and fluid collections are quite common in morbidly obese patients. These complications are often exacerbated by the presence five or six inches of fatty tissue outside the muscle layers of the abdomen.

Complications that occur later on after the incision is all healed include narrowing of the stoma (the junction between stomach pouch and intestine), which results from scar tissue development. Recall that this opening is made about 10 mm in diameter, not much wider than dime. With an opening this small, a very little scarring will squeeze the opening down to a degree that affects the patient's eating. Vomiting which comes on between the 4th and 12th week may well be due to this cause. The problem can be very simply dealt with by stretching the opening to the correct size, by "endoscopic balloon dilatation", which usually involves a single procedure on a day stay basis to correct the problem. Wound hernias occur in 5-10% and intestinal obstruction in 2% of patients an incidence similar to that following any general surgical abdominal procedure.

Another late problem that is fairly common, especially in menstruating women, after gastric bypass is anemia. Since the stomach is involved in iron and Vitamin B12 absorption, these may not be absorbed adequately following bypass. As a result anemia may develop. The patient feels tired and listless, and blood tests show low levels of hematocrit, hemoglobin, iron and Vitamin B12. The condition can be prevented and treated, if necessary, by taking extra iron and B12. Since the food stream bypasses the duodenum, the primary site of calcium absorption, the possibility of calcium deficiency exists, and all patients should take supplemental calcium to forestall this.

Dumping is often mentioned as a complication of gastric bypass, but it really is a side effect of the procedure caused by the way the intestine is hooked up. Dumping occurs when the patient eats refined sugar following gastric bypass, this causes symptoms of rapid heart beat, nausea, tremor and faint feeling, sometimes followed by diarrhea. Of course no one likes these feelings, especially patients who love sweets! The upshot is, of course, that sweet lovers avoid sweets after gastric bypass and this is a real help to them in their efforts to lose weight. It should be noted that a few surgeons, expert at endoscopic/laparoscopic surgery, are performing Gastric Bypass using laparoscopic techniques.

Listing of complications following gastric bypass:

Early:
1. Leak
2. Acute gastric dilatation
3. Roux-Y obstruction
4. Atelectasis
5. Wound Infection/seroma Late:
1. Stomal Stenosis
2. Anemia
3. Vitamin B12 deficiency
4. Calcium deficiency/osteoporosis Silastic Ring Gastric Bypass & Vertical banded gastric bypass (Fobi): The use of rings to control the stoma size, proven with Vertical Banded Gastroplasty, has led to their adoption by some surgeons as an addition to gastric bypass procedures, again to control the stoma size and prevent late stretching of the opening and, hopefully, improve the long term weight maintenance results. Both silastic rings and Marlex bands have been used. Usually the recommendation is for the ring circumference to be considerably larger than that used in primary obesity procedures, so that the limiting effect only comes into play after some degree of stretching of the pouch has occurred. The complications following silastic ring gastric bypass include the same complications as for gastric bypass, plus band erosion.

GASTROPLASTY: During World War II, the Russians, as part of their war effort, developed a series of surgical instruments to staple various body tissues together as a simple and rapid method of dealing with injuries. This concept was adapted and refined by American surgical instrument makers after the war, leading to the surgical stapling instruments in use today. These are capable of laying down as many as four parallel rows of staples, to create a partition, or the instrument comes with a knife blade which will cut between the newly placed staple rows, dividing and sealing the stapled tissues simultaneously. Other instruments place circular rows of staples to join two tubes end-to-end, which is very useful in connecting intestine together.

The early use of such stapling devices in obesity surgery involved removal of three staples from the row and firing the stapler across the top part of the stomach. This staples the two stomach walls together, except at the point where the three staples were removed, where a small gap remains. The idea being that food that the patient takes in is held up in the segment of stomach above the staple line causing the sensation of fullness. The food then empties slowly through the gap (stoma) into the stomach below the staple line where digestion takes place normally. Unfortunately, the muscular stomach wall has a tendency to stretch and the stoma enlarges. It soon became apparent that while patients lost weight for the first few months while the stoma was small, they soon stopped losing, and, indeed, frequently regained all they had lost. Surgeons tried to counter this by reinforcing the opening between the two compartments (Gomez 1981), however these techniques were only partially successful. The search for a better gastroplasty was pursued by Dr. Edward E. Mason, Professor of Surgery at the University of Iowa. (Mason 1982) He realized that the lesser curvature part of the stomach had the thickest wall and was therefore least likely to stretch, so he used a vertical segment of stomach along the lesser curvature for the pouch. Additionally, he was very meticulous in defining the size of the pouch, measuring it at surgery under a standard hydrostatic pressure, and has shown that best results follow the use of a very small pouch, holding only 14 cc saline at the time of surgery. The third modification that he made was to place a polypropylene band (Marlex Mesh) around the lower end of the vertical pouch, which acts as the stoma, to fix the size of the outlet of the pouch, preventing it from stretching. This is done by use of the circular stapling instrument to staple the front and back walls of the stomach together, cutting out a circular window to allow the polypropylene band to be placed around the lower end of the pouch. His extensive studies showed that the correct circumference of the band is 5.0 cm. The whole operation is called Vertical Banded Gastroplasty (VBG). Correctly performed this operation produces good weight loss results. It has the advantages of being a pure restrictive procedure with no malabsorption component and no dumping. Of course sweet eaters will have to avoid sweets on their own if they have this procedure. Similarly there are few complications associated with Vertical Banded Gastroplasty, because all food taken in is digested normally, and anemia is rare and Vitamin B12 deficiency is almost unknown. The patient does have to be very careful to chew food completely to avoid vomiting, and to avoid high calorie liquids such as regular sodas and ice cream that pass easily through the stoma. A surgical variant of the VBG is the Silastic Ring Vertical Gastroplasty (SRVG), which is functionally identical to VBG but uses a silastic ring to control the stoma size. It should be noted that a few surgeons, expert in minimal access surgery are performing gastroplasty using laparoscopic techniques.

Listing of complications following vertical banded gastroplasty:

Stenosis with persistent vomiting, if untreated, causing neurological damage

Ulcer

Incisional hernia

Wound Infection

Band erosion

Leakage (including post-operative leakage due to failure of the initial closure and late leakage due to staple line failure and/or failure of the stomach walls to heal/fuse together)

GASTRIC BANDING: Another way to limit food intake is to place a constricting ring completely around the top end (fundus) of the stomach, creating an hourglass effect. The ring is placed near the upper end of the stomach, just below the junction of stomach and esophagus. This idea of gastric banding has been around for quite a number of years, and was pursued in Europe and Scandinavia particularly. Initially, a readily available material such as arterial graft was used for the band. The results, however, were not as good as RGB or VBG and the concept has only become popular with the development of modern bands designed for the task and techniques to measure the size of the "stoma" created under the band and associated pressures. An ingenious variant, the inflatable band was developed by Dr. Kuzmak (Kuzmak, Yap et al. 1990) who devised a band lined with an inflatable balloon. This balloon was connected to a small reservoir that is placed under the skin of the abdomen, through which, the balloon can be inflated, thus reducing the size of the stoma, or deflated thus enlarging the stoma. Even more ingenious, has been the development of models that can be inserted laparoscopically, thus saving the patient the discomfort of a large incision. Since the hourglass configuration only constricts the upper stomach, with no malabsorptive effect, it acts as a pure restrictive operation. Like VBG, the favorable consequences are absence of anemia, dumping and malabsorption, while the disadvantages include the need for strict patient compliance. Long-term results of this device are not yet available, but logic would suggest they are likely to be comparable to VBG results with an unknown additional effect due to manipulation of the inflatable balloon. At the present time there are two devices on the world market. The LapBand manufactured by Bioenterics, Carpenteria, Calif. and the Obtech device produced in Sweden by Obtech Medical AG. Only the LapBand is freely available in the USA at this time, having completed U.S. trials and been approved for use by the FDA.

Listing of Complications Following Gastric Banding

Operative:

Splenic Injury

Esophageal Injury

Conversion to Open Procedure

Wound Infection

Late:

Band slippage

Reservoir deflation/leak

Failure to lose weight

Persistent vomiting

Acid reflux

PRIOR ART

Smit (U.S. Pat. No. 4,134,405, U.S. Pat. No. 4,315,509), Berry (U.S. Pat. No. 5,306,300) and Crabb (U.S. Pat. No. 5,820,584) have described intestinal sleeves, however the opening of these sleeves were placed within the stomach with their openings allowing entry of gastric secretions into the tube where they could mix with the ingested food. Rockey (U.S. Pat. No. 4,501,264, U.S. Pat. No. 4,641,653, U.S. Pat. No. 4,763,653) describes a sleeve which is in the stomach or the intestines and which works by "reducing the surface area of the digestive tract".

All of these patents discuss reduction of caloric intake and/or reduced digestion efficiency. These statements are not correlated with discussions of a requisite length of sleeve to accomplish these ends. It is well know that clinically a person can receive sufficient nutrition with a small fraction of their intestines remaining. With a length of 20-30 feet, or more, of intestine in man a sleeve or tube functioning as described in these patents may require a length of 10-20 ft or more.

Berry has a discussion of gastric bypass for treatment of obesity, however his patent focuses an alternative to this procedure rather than building upon the successes of the surgical treatments. None of this art contemplates a combination with a gastric restrictive procedure nor do they discuss a mode of operation that would be effective in reducing weight at a sleeve length of 2-6 feet.

SUMMARY OF THE INVENTION

In keeping with the foregoing discussion, the present invention provides apparatus and methods that can be applied using minimally invasive techniques for treatment of morbid obesity. The apparatus takes the form of a system of components that may be used separately or in combination for effectively reducing stomach volume, bypassing a portion of the stomach and/or small intestines, reducing nutrient absorption in the stomach and/or small intestines and depositing minimally or undigested food farther than normal into the intestines (thereby stimulating intestinal responses).

The first major component of the system is an artificial stoma device located in the stomach or lower esophagus that reduces the flow of food into the stomach (when located in the stomach) or back from the stomach into the esophagus (when located in the esophagus or at the gastroesophageal junction). Alternatively, the system may utilize a surgically created artificial stoma. Stomas that prevent flow of gastric contents into the esophagus can be used in the treatment of Gastro Esophageal Reflux Disease (GERD). The stoma is introduced transesophageally and implanted under visualization with a flexible endoscope. The stoma may be anchored to the esophageal or stomach wall using sutures, staples or clips. Alternatively, the stoma may be anchored with a sutureless attachment that does not penetrate the esophageal or stomach wall. Optionally, multiple stomas can be installed, e.g. one for GERD and one for restriction of food passage. Optionally, the stoma may be used in conjunction with gastric suturing, stapling or banding to create a narrow passage for installation of the stoma and/or for reduction of gastric volume. The gastric stapling or banding may be applied using transesophageal or laparoscopic techniques. Optionally the stoma may be in multiple parts where the parts may be individually placed, replaced or exchanged. Optionally, the stoma may have an adjustable opening to vary the flow of food through the stoma and/or allow the passage of diagnostic or therapeutic devices such as endoscopes. The adjustable stoma may be adjusted at the time of implantation or it may be adjustable remotely after implantation without invasive procedures. Alternatively, the stoma may be a self-adjusting "smart stoma" that opens and/or closes in response to stomach conditions.

The second major component of the system is an internal gastric sleeve that may be used separately or used with, attached to or integrated with the artificial stoma component. The gastric sleeve may have a funnel-shaped entry with a reinforced anchoring segment or other anchoring mechanism for attachment in the stomach at or near the gastroesophageal junction. Optionally, the artificial stoma component may be positioned at the base of the funnel-shaped entry. When placed in the stomach, the internal funnel shape entry effectively reduces the volume of the stomach because the flow of solid food is limited to the lumen of the funnel. When combined with a restrictive stoma, the funnel functions as the pouch in a gastric bypass or vertical banded (or other) gastroplasty. The funnel can be designed and placed to maximize the amount of stomach wall included by the funnel opening and therefore included in the pouch thereby formed. This will enable a maximum number of stretch receptors and other stimulating mechanisms in the stomach to transmit satiety (fullness) signals to help reduce food intake.

The entire gastric sleeve or a portion of it can be porous or semipermeable to allow the flow of digestive secretions into the sleeve and to allow the flow of nutrients and/or fluids out through the wall of the gastric sleeve. Valves may be provided in the wall of the gastric sleeve to allow digestive secretions to enter the sleeve, but to prevent solid food and/or nutrients from flowing out through the wall of the sleeve. Alternatively, the entire gastric sleeve or a portion of it can be nonporous or impermeable to act as an internal gastric bypass. The wall of the gastric sleeve is preferably flexible to allow the peristaltic motions of the stomach to effect movement of food through the gastric sleeve. The wall of the sleeve may be reinforced with rings or a spiral made of wire and/or plastic. Alternatively, the gastric sleeve may be attached to an artificial stoma component that includes its own anchoring mechanism. Optionally, the distal end of the gastric sleeve may be anchored in the region of the pylorus.

In conjunction with the stoma and/or gastric sleeve, the volume of the stomach can be reduced by suturing, stapling using open, transesophageal or laparoscopic techniques. Alternatively or in addition, a gastric balloon or other volume displacement device may be used in conjunction with the gastric sleeve to provide a feeling of satiety. These adjunctive techniques have the effect of further reducing nutrient intake (in the case of a stomach reduction and pouch formation upstream of a stoma) and enhancing the effect of peristaltic motions of the stomach for moving food through the gastric sleeve intake (in the case of a stomach reduction downstream of a stoma where there is a gastric sleeve).

One advantage of using an internal gastric sleeve over prior art gastric volume reduction techniques is that volume reduction can be better defined in that the patient cannot deliberately or inadvertently increase the volume of the sleeve over time by overeating as occurs when the stomach wall stretches.

The third major component of the system is an internal intestinal sleeve that may be used separately or used with, attached to or integrated with the internal gastric sleeve and/or artificial stoma component. The entire intestinal sleeve or a portion of it can be porous or semipermeable to allow the flow of digestive secretions into the sleeve and to allow the flow of nutrients and/or fluids out through the wall of the sleeve. Valves may be provided in the wall of the intestinal sleeve to allow digestive secretions to enter the sleeve, but to prevent solid food and/or nutrients from flowing out through the wall of the sleeve. Alternatively, the entire intestinal sleeve or a portion of it can be nonporous or impermeable to act as an internal intestinal bypass. The wall of the intestinal sleeve is preferably flexible to allow the peristaltic motions of the intestinal wall to effect movement of food through the intestinal sleeve. The wall of the sleeve may be reinforced with rings or a spiral made of wire and/or plastic. Optionally these components can include radiopaque materials for visualization of the device when it is in the body.

Optionally, the intestinal sleeve may have a proximal end with a reinforced anchoring segment or other anchoring mechanism for attachment in the region of the pylorus. Alternatively, the intestinal sleeve may be attached to or continuous with the internal gastric sleeve. Optionally, the distal end of the intestinal sleeve may include an anchoring mechanism.

Optionally, the above system components can include means of separately installing, replacing and/or removing single components. This would include means of reversibly attaching and connecting components. This would allow a therapeutic device to be assembled over multiple operations or in a single procedure. Alternatively, the above components can be preassembled with a specific combination of desired features for an individual patient and thereby installed and removed in a single operation. Preferably, each component of the system includes one or more radiopaque and/or sonoreflective markers for enhanced imaging by X-ray, fluoroscopy and/or ultrasonic imaging.

Advantages over the prior art:
1. Minimally invasive, peroral/transesophageal implantation, with optional laparoscopic assist
2. Customizable to each patient and revisable in-situ based upon the results of the intervention
3. Completely reversible using minimally invasive techniques
4. Lower morbidity, mortality
5. When used with a gastric and/or intestinal sleeve, does not allow appreciable amount of digestion to occur until the food exits the sleeve into the intestine by keeping food separate from gastric and/or intestinal secretions. This delivers undigested food to the jejunum where a dumping syndrome reaction and other results of overstimulation of the intestine can occur.

BRIEF DESCRIPTION OF THE DRAWINGS

FIG. 3 shows an enlarged view of an artificial stoma device with a variable diameter stoma aperture.

FIGS. 4A-4B shows an alternate embodiment of an artificial stoma device with a variable diameter stoma aperture.

FIGS. 5A-5B show an adjustable stoma with an inflatable bladder, pump and reservoir and with optional suture anchors.

FIGS. 10A-10C show an artificial stoma device with a sutureless anchoring mechanism.

FIG. 17 shows an artificial stoma device implanted within a patient's stomach with a line of gastroplasty sutures or staples to reduce the gastric volume. Also shown is a line of sutures or staples longitudinally dividing the small intestine to create a biliopancreatic channel separate from the intestinal lumen.

FIG. 18 shows a cross section of the patient's small intestine showing the biliopancreatic channel.

DETAILED DESCRIPTION OF THE PREFERRED EMBODIMENT

The present invention provides apparatus and methods for treatment of morbid obesity. The apparatus takes the form of a system of components that may be used separately or in combination for effectively reducing stomach volume, bypassing a portion of the stomach and/or small intestines and reducing nutrient absorption in the stomach and/or small intestines. Each of the components can be implanted using minimally invasive techniques, preferably using a transesophageal approach under visualization with a flexible endoscope. Optionally, laparoscopic surgical techniques may be used to assist in the implantation of the components and/or for adjunctive therapies in the digestive tract.

Figure 1:
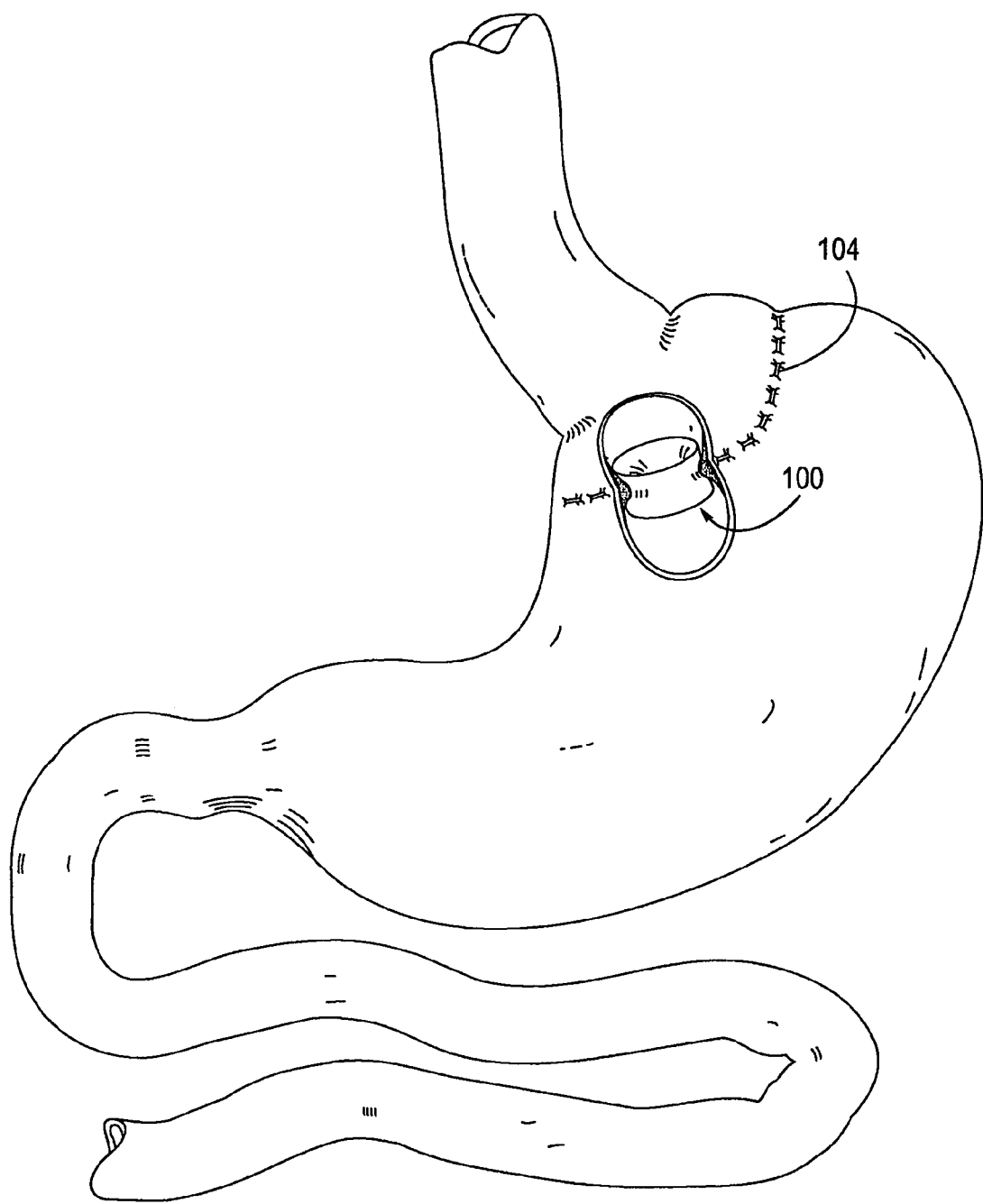
FIG. 1 shows an artificial stoma device implanted within a patient's stomach with a line of gastroplasty sutures or staples to create a narrow passage.

The first major component of the system is an artificial stoma 100 located in the stomach or lower esophagus that reduces the flow of food into the stomach. FIG. 1 shows an artificial stoma device 100 implanted within a patient's stomach. The stoma device 100 is introduced transesophageally and implanted under visualization with a flexible endoscope. The stoma may be anchored to the esophageal or stomach wall using sutures, staples, clips or other anchoring mechanisms. Optionally, the stoma 100 may be used in conjunction with gastric suturing, stapling or banding to create a narrow passage for installation of the stoma and/or for reduction of gastric volume. The gastric suturing, stapling or banding may be applied using transesophageal or laparoscopic techniques. In the exemplary application shown in FIG. 1, a line of gastroplasty sutures or staples 104 has been used to create a small gastroplasty pouch with a narrow passage for installation of the stoma 100. The gastroplasty sutures or staples 104 may be applied using transesophageal or laparoscopic techniques.

The artificial stoma 100 may include a fabric cuff on the outer circumference to facilitate ingrowth of tissue to secure the stoma device 100 in place. In-growth can be further facilitated by partial transection of the gastric wall through the mucosa. This will put the fabric cuff in contact with muscularis. Alternatively or in addition, a number of suture attachment points can be included on the outer circumference of the stoma device. The suture attachment points may take the form of suture attachment loops attached to the outer circumference of the stoma device or a ring with suture attachment holes formed in it.

In a preferred embodiment the outer circumference of the stoma 100 is flexible and elastic with properties to minimize the resistance of the stoma 100 to motion of the stomach at the stomal attachment points. This also serves to minimize the forces that can lead to tissue erosion.

Figure 2A:
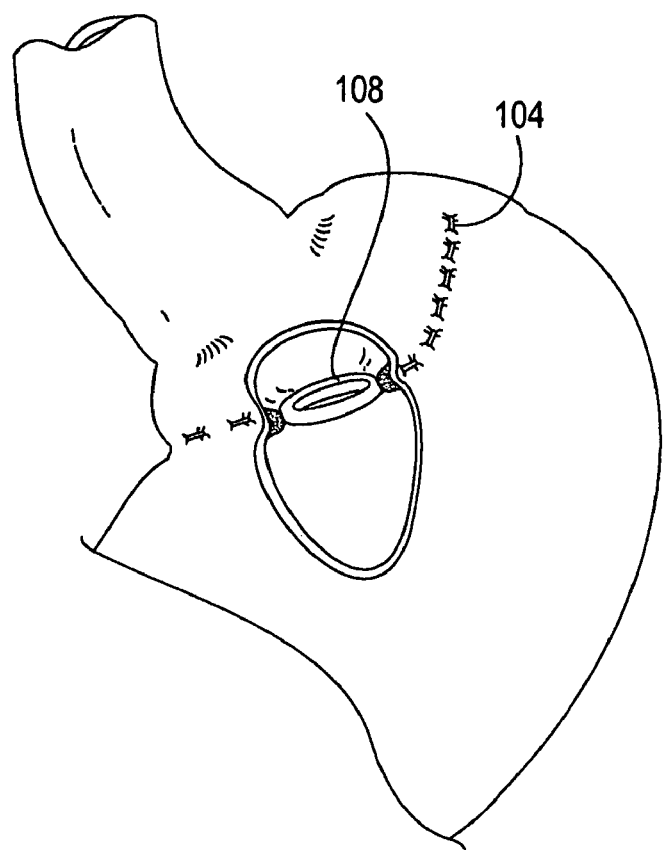
FIGS. 2A-2B shows a stoma device with a separate anchoring device in the form of an anchoring ring.
Figure 2B:
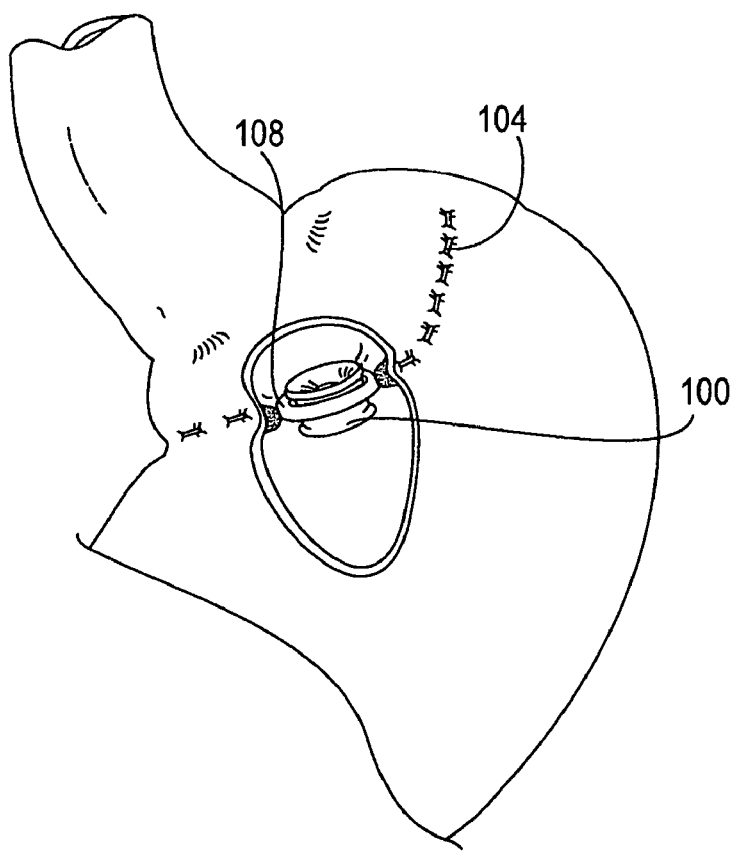

In an alternative embodiment, the artificial stoma device may include a separate anchoring device that may be in the form of an anchoring ring or a series of anchoring points for attachment to the gastric or esophageal wall. FIGS. 2A-2B shows a stoma device 100 with a separate anchoring device in the form of an anchoring ring 108. The anchoring ring 108 may include a sutureless anchoring mechanism and/or a fabric cuff or other attachment points for sutures, staples, clips or other anchoring mechanisms. The anchoring device 108 is initially implanted in the stomach or lower esophagus, as shown in FIG. 2A. Preferably, the tissue is allowed to heal for a number of weeks before the artificial stoma 100 is installed by attaching it to the anchoring device 108 in a subsequent procedure, as shown in FIG. 2B.

Optionally, the stoma 100 may have an adjustable opening 110 to vary the flow of food through the stoma. FIG. 3 shows an enlarged view of an artificial stoma device 100 a variable diameter stoma aperture 110. The adjustable stoma 100 may be adjusted at the time of implantation and/or it may be adjustable remotely after implantation without invasive procedures.

The adjustable stoma 100 is preferably formed as a cylinder that can be collapsed for insertion, and then expanded when in place. Preferably, the outer diameter will maintain a set, but somewhat elastic, diameter to facilitate fixation in the body. The outer circumference may be supported by a metal lattice 114 that is deformed permanently by the initial deployment. Possible materials for the metal lattice 114 include 304 and 316 stainless steel. Deployment can be by a coaxial balloon catheter.

The inner circumference of the adjustable stoma is preferably supported by a metal lattice 116 made of a NiTi alloy where the deformation needed to deploy the device and set the size of the inner diameter can be reversed by the application of heat. Heat could be applied by a balloon catheter with circulating heated fluid, RF energy or other known means. The NiTi lattice 116 can then be expanded to the desired diameter by a balloon catheter inflated in the stoma aperture 110.

The entire adjustable stoma 100 is covered by a biocompatible material 118, preferably an elastomer, to prevent ingress of fluids into the interior of the adjustable stoma 100. Examples of suitable materials include silicone (e.g. Dow Silastic or similar material from Nusil) and polyurethane (e.g. Dow Pellethane). The outer circumference is adapted for accepting sutures or staples for attachment within the body.

FIGS. 4A-4B shows an alternate embodiment of an artificial stoma device 100 with a variable diameter stoma aperture 110. The inner circumference of the adjustable stoma is supported by a wire coil 126 that helps to maintain the adjustable stoma aperture 110. The wire coil 126 is preferably made of a shape-memory NiTi alloy, so that the stoma aperture 110 can be adjusted larger or smaller using the method described below. Alternatively, the wire coil 126 may be made of a material that is plastically deformable, such as stainless steel, to adjust the stoma aperture 110 larger using a dilator, such as an inflatable balloon. Stomas of this type are preferably inserted in a collapsed state to facilitate passage through the esophagus. This type of stoma and other collapsible stomas can utilize a removable sleeve or other means for temporarily holding the stoma in the collapsed state.

Any of the stoma devices described herein can be placed in the lower esophagus to prevent reflux. Esophageal stomas will preferably be configured to allow one-way flow and seal against or resist retrograde flow. This could be accomplished with a smart type stoma, preferably one that closes in response to gastric secretions, or a one-way valve, such as a duckbill or flap type valve.

The stoma device 100 may be implanted and adjusted according to the following method:

Stoma Placement 1) place oral-gastric tube into the patient's stomach, the oral-gastric tube can optionally include a separable sleeve;

2) insert a guidewire through the oral-gastric tube into the stomach;

3) remove the oral-gastric tube, optionally, the sleeve may be left in place to protect the esophagus;

4) position the adjustable stoma over the balloon on a primary dilatation catheter;

5) insert the dilatation catheter and the adjustable stoma over the guidewire into the stomach;

6) inflate the balloon oh the dilatation catheter to expand the adjustable stoma;

7) exchange the dilatation catheter and repeat if necessary to achieve the proper outer diameter;

8) suture or staple the stomach wall to approximate a gastric pouch, this can be done with open surgery, laparoscopically or, preferably, transesophageally;

9) reinflate the balloon on the dilatation catheter to grip the adjustable stoma;

10) withdraw the dilatation catheter until the adjustable stoma is positioned within the suture line in the desired stoma position;

11) secure the adjustable stoma in place and suture, staple and/or glue to seal the adjustable stoma to the gastric pouch;

12) withdraw the dilatation catheter;

13) insert the heat application means over the guidewire and position it within the stoma aperture;

14) apply heat to shrink the inner diameter of the adjustable stoma;

15) withdraw the heat application means;

16) if necessary, insert a dilatation catheter and inflate the balloon to dilate the stoma aperture to the desired diameter;

17) withdraw the dilatation catheter and guidewire.

This method can be modified for installation of a fixed diameter stoma device or a smart stoma device that does not require heating and/or dilatation to adjust the inner diameter of the stoma aperture. The method can also be modified for installation of a stoma device with a self-expanding metal lattice on the outer circumference, obviating the need for the primary dilatation catheter. The order of the method can also be modified, for example the pouch can be created first or the artificial stoma can be placed in a pre-existing pouch where the surgically created stoma has become enlarged.

The adjustable stoma device may be initially implanted with the stoma aperture larger than clinically useful. This would allow food to pass easily through the stoma aperture and minimizes the stress on the attachment points for the stoma device and the sutures or staples forming the gastric pouch. This will allow the stomach wall to heal before the stoma aperture is reduced to a clinically significant diameter, which will naturally place more stress on the tissue and the attachment points.

Alternatively, the adjustable stoma 100 may be configured such that the inner diameter 110 is adjusted by inflation by transferring fluid from a reservoir into the annulus between the inner and outer circumference. FIGS. 5A-5B show an adjustable stoma 100 with an inflatable bladder 120, pump 122 and reservoir 124 and with optional suture anchors 112.

Figure 6A:
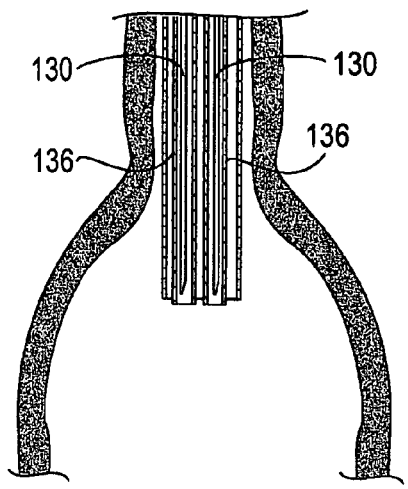
FIGS. 6A-6D show wire fasteners useful for attaching the stoma device and forming a gastroplasty pouch.
Figure 6B:
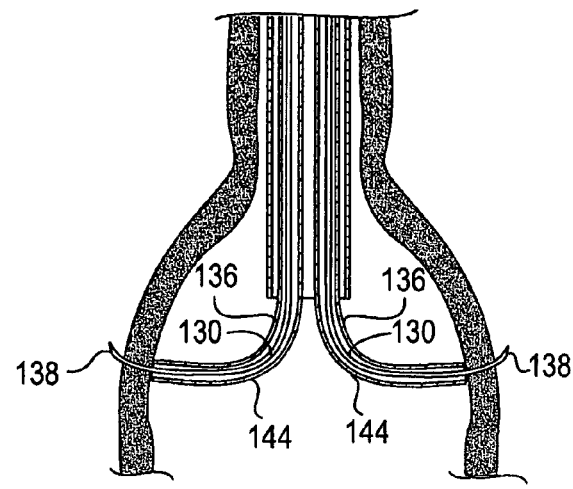
Figure 6C:
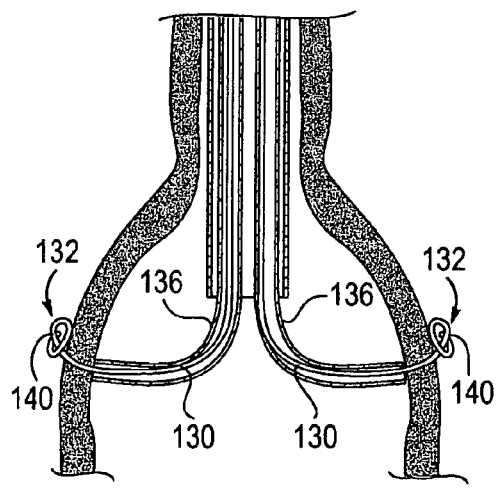
Figure 6D:
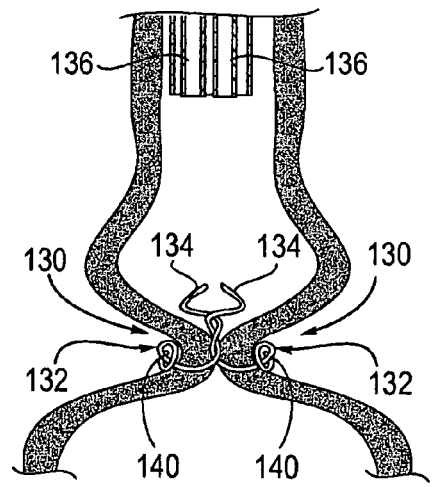

Stapling or suturing for placement of the adjustable stoma device 100 is preferably accomplished transesophageally with the use of a flexible endoscope. One method for accomplishing this involves the use of wire fasteners 130 that are formed with a "button" end 132 and a "twist tie" end 134, which are shown in FIGS. 6A-6D. The wire fasteners 130 are preferably formed from a superelastic NiTi alloy so that the fasteners can be straightened out and passed through a delivery cannula 136, as shown in FIG. 6A. The distal tip 138 of the wire is sharpened so that it will penetrate tissue. A portion of the distal end of the wire is formed so that it will assume a circular or spirally curled "button" shape 132 after it has passed through the tissue, as shown in FIG. 6B. The "button" shape 132 attaches the fastener to the stomach wall and prevents it from being pulled out through the tissue. The curl of the "button" 132 is preferably shaped so that it protects the sharpened distal tip 138 of the wire and prevents it from damaging the stomach wall or surrounding tissues after the fastener is deployed. There is an approximately 90 degree bend 140 in the wire just proximal to the "button" portion 132. A portion of the proximal end of the wire is formed to create the "twist tie" 134, which reforms when the wire fastener 130 is pushed out of the delivery cannula 136, as shown in FIG. 6C. The "twist tie" 134 is preferably a helical curl or other shape that will entangle and interlock with a mating fastener when the two are approximated to one another, as shown in FIG. 6D. Alternately, the proximal end 134 of the wire fastener 130 can form a loop for attachment of standard suture materials.

The delivery cannula 136, which preferably has a torquable shaft with a fixed or variable curve 144 at the distal end, is used to deliver the wire fasteners 130 to the desired location. The distal end of the delivery cannula 136 is advanced until it contacts the stomach wall, then a pusher wire or the like is used to advance the wire fastener 130 through the delivery cannula 136, as shown in FIG. 6A. As the wire fastener 130 exits the delivery cannula 136, the sharpened distal tip 138 penetrates the stomach wall. The "button" portion 132 of the wire assumes its curved con-figuration distal to the stomach wall as the fastener 130 is advanced farther out of the delivery cannula 136, as shown in FIG. 6B. These steps are repeated to place a second wire fastener 130 in the opposite wall of the stomach. Then, the two delivery cannulas 136 are withdrawn while continuing to advance the wires out of the delivery cannulas to allow the "twist tie" portions to assume their helical curled shape proximal to the stomach wall and the two fasteners are approximated to one another so that the two "twist tie" portions intertwist with one another as they exit the delivery cannulas to attach the two walls of the stomach together, as shown in FIG. 6D. Alternatively, the wire fasteners 130 can employ a loop, rather than a "twist tie" to enable approximation using a secondary means such as sutures. A line of fasteners 130 can be thus deployed to create a gastroplasty pouch or band.

In an alternate embodiment, the wire fasteners may be configured to have a "button" portion 132 on both ends of the wire. These fasteners can be deployed laparoscopically to penetrate both walls of the stomach with a "button" 132 placed on each side of the stomach to attach the walls together.

Another method of intragastric stapling utilizes a pair of vacuum or mechanical graspers to capture the tissue to be joined, for example the stomach wall. The graspers approximate the tissue and present it to a stapling mechanism. Once the tissue has been presented to the stapling mechanism, a number of methods may be used:

1) a staple or clip may be applied to join the tissue together;

2) a precurved wire fastener, which may be constructed of a NiTi alloy or other material, may pierce the tissue on one side and then pierce the tissue on the other side as it curls to capture both;

3) a curved needle with attached suture can be passed through the tissue using known endoscopic suturing techniques.

These two methods (vacuum approximation and NiTi buttons) can also be combined.

Figure 7A:
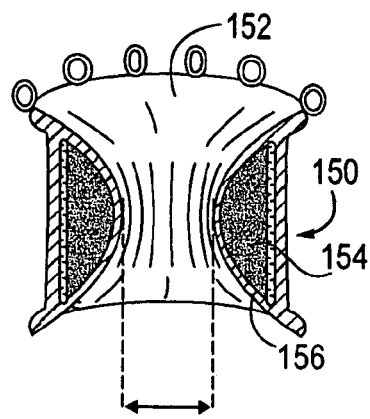
FIGS. 7A-7B show an enlarged view of a smart stoma device with a stoma aperture that varies its diameter in response to conditions in the patient's stomach.
Figure 7B:
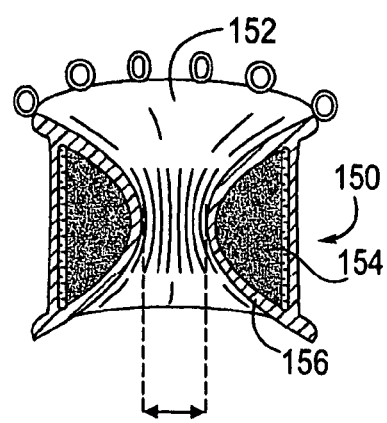

In an alternative embodiment, the stoma may be a self-adjusting "smart stoma" that opens and/or closes in response to stomach conditions. FIGS. 7A-7B show an enlarged view of a smart stoma device 150 with a stoma aperture 152 that varies its diameter in response to conditions in the patient's stomach. In one preferred embodiment shown in FIGS. 7A-7B, the smart stoma device 150 includes a fluid-filled bladder 154 surrounded by an osmotic membrane 156. One example of a suitable material for the osmotic membrane 156 is silicone. The osmotic membrane 156 may be made of microporous silicone or other material similar to those used for hemodialysis membranes. In response to changing conditions, for example if the patient drinks a glass of water, water will move across the osmotic membrane 156 to swell the bladder 154 and shrink the stoma aperture 152 to restrict food intake.

Figure 8A:
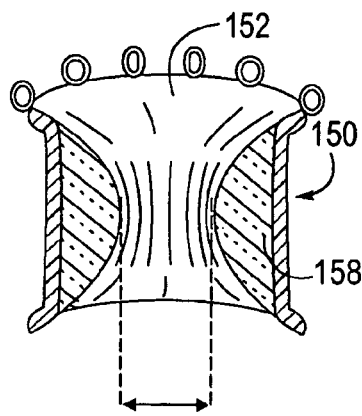
FIGS. 8A-8B show another embodiment of a smart stoma device with a stoma aperture that varies its diameter in response to conditions in the patient's stomach.
Figure 8B:
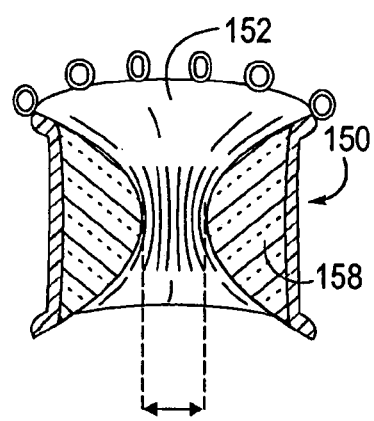

In another embodiment shown in FIGS. 8A-8B, the smart stoma device 150 may include a toroidal member 158 made of a swellable material, such as a hydrogel. In response to changing conditions, for example if the patient drinks a glass of water, the toroidal member 158 will swell and shrink the stoma aperture 152 to restrict food intake.

Figure 9A:
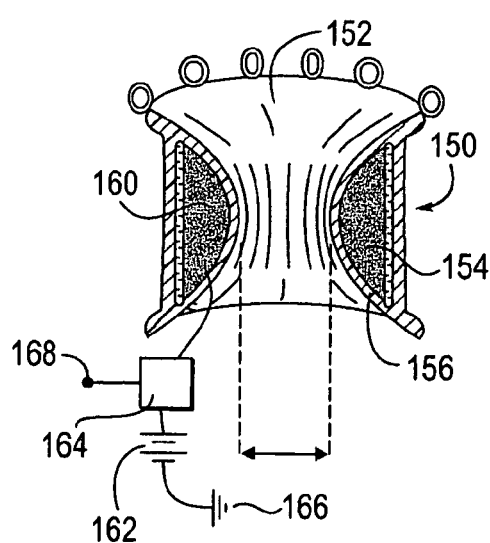
FIGS. 9A-9B show an enlarged view of a smart stoma device with a closed loop controlled variable diameter stoma aperture.
Figure 9B:
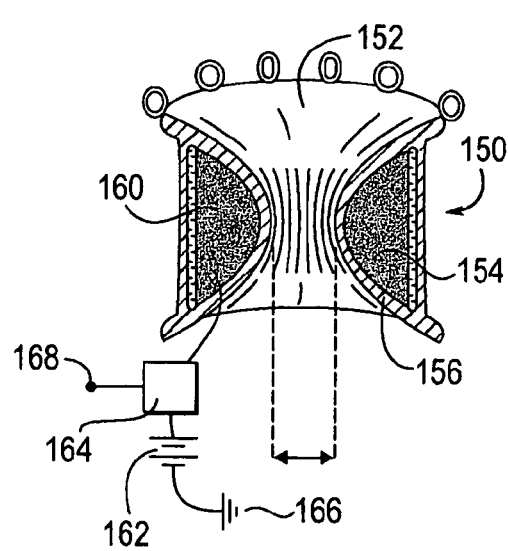

FIGS. 9A-9B show an enlarged view of a smart stoma device 150 with a closed loop controlled variable diameter stoma aperture. Similar to the embodiment shown in FIGS. 7A-7B, this smart stoma device 150 includes a fluid-filled bladder 154 surrounded by an osmotic membrane 156. A first electrode 160 is connected to the osmotic membrane 156. The first electrode 160 and a ground electrode 166 placed elsewhere on the body are connected to a voltage source 162 such as a battery via a control circuit 164. When a voltage is applied between the first electrode 160 and the ground electrode 166, it increases the flow rate across the osmotic membrane 156 to quickly swell the bladder 154 and shrink the stoma aperture 152 to restrict food intake. Note that the polarity of the circuit in FIGS. 9A-9B is for reference only and can be altered based on material selection and fluid polarity. The stoma device 150 may be configured to operate automatically in response to changing conditions, for example the control circuit 164 may include a sensor 168 for sensing water or certain nutrients, such as sugar, or an activity related to ingestion, such as swallowing or gastric response. Alternatively, the stoma device 150 may be configured to be remotely operated in response to a control signal from outside of the patient's body.

Alternatively, the artificial stoma may be anchored with a sutureless attachment that does not penetrate the esophageal or stomach wall. Sutureless attachment mechanisms may be used in conjunction with any of the stoma configurations discussed herein. FIGS. 10A-10C show an artificial stoma device 170 with a sutureless anchoring mechanism 172. The stoma device 170 has a retracted/compressed position wherein the stoma device 170 and the anchoring mechanism 172 have a small diameter that can easily pass through the patient's esophagus into the stomach, as shown in FIG. 10A. The stoma device 170 may be introduced mounted on a flexible endoscope or on a separate insertion device. Once the stoma device 170 is in the selected position in the stomach or lower esophagus, the sutureless attachment mechanism 172 is actuated to expand and hold the stoma device 170 in place, as shown in FIGS. 10B and 10C.

In one embodiment, the sutureless attachment mechanism 172 may be configured as an expandable wire stent that expands against the stomach or esophageal wall to hold the stoma device 170 in place. Preferably, the expandable wire stent is surrounded by an elastomeric membrane or the like to prevent leakage of liquids or food past the stoma device 170. The surface of the membrane may be treated to encourage tissue ingrowth to permanently anchor the stoma device 170 in place. Alternatively, or in addition, the sutureless attachment mechanism 172 may include barbs that pierce the tissue for additional anchoring. In an alternative embodiment, the stoma device 170 may be configured to have a reversible sutureless attachment mechanism 172 for temporary implantation of the device.

A reversible sutureless attachment mechanism 172 may have two modes of attachment, a temporary mode and a permanent mode. Thus, a stoma device 170 can be implanted in a patient's stomach for a trial period using the temporary attachment mode. After the trial period, if the therapy has been ineffective or if the implant was not well tolerated by the patient, the stoma device 170 can be removed. On the other hand, if the therapy has been effective and the implant is well tolerated by the patient, the stoma device 170 can be permanently attached by actuating the permanent attachment mode or simply leaving the implant in place to allow permanent attachment and tissue ingrowth to take place.

Preferably, the stoma device is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted stoma device can be verified noninvasively.

Figure 11:
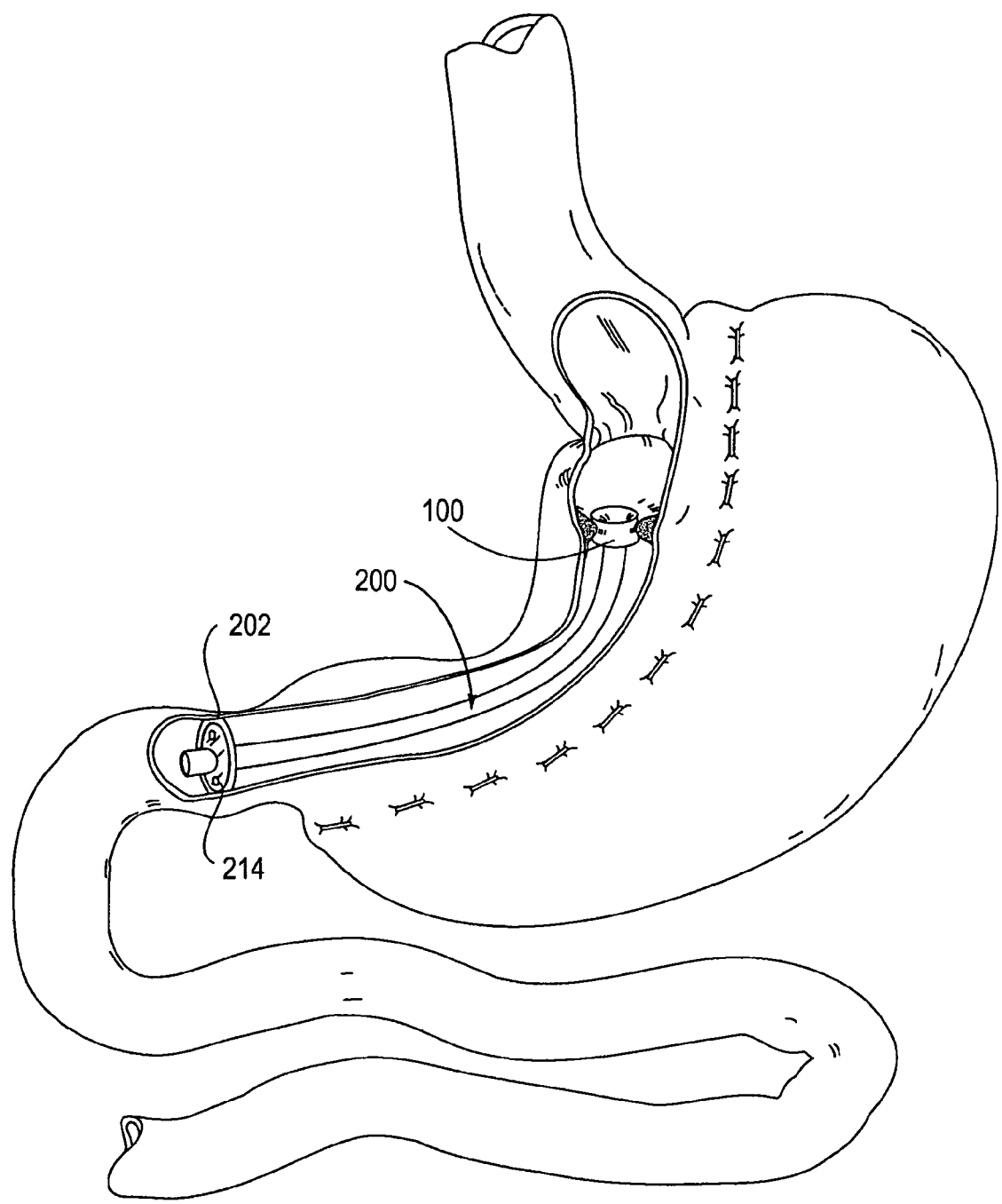
FIG. 11 shows a gastric sleeve device with an artificial stoma device and a pyloric sleeve anchor implanted within a patient's stomach with a line of gastroplasty sutures or staples parallel to the sleeve.

The second major component of the system is an internal gastric sleeve 200 that may be used separately or used with, attached to or integrated with the artificial stoma component 100. FIG. 11 shows a gastric sleeve device 200 with an artificial stoma device 100 implanted within a patient's stomach. Optionally the sleeve can be attached to the outlet of a surgically created stoma or pouch that does not include an artificial implanted stoma. Preferably, the gastric sleeve device 200 includes a pyloric sleeve anchor 202 for anchoring the distal end of the sleeve 200 in the region of the pylorus. The pyloric sleeve anchor 202 is preferably configured with openings 214 to allow digestive secretions to pass through the pylorus into the small intestine. The internal gastric sleeve 200 effectively reduces the volume of the stomach because the flow of solid food is limited to the lumen of the sleeve 200. The entire gastric sleeve 200 or a portion of it can be porous or semipermeable to allow the flow of digestive secretions into the sleeve and to allow the flow of nutrients and/or fluids out through the wall of the gastric sleeve 200.

Figure 12A:
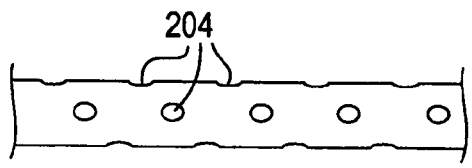
FIGS. 12A-12E are detail drawings showing additional features of a gastric or intestinal sleeve device.
Figure 12B:
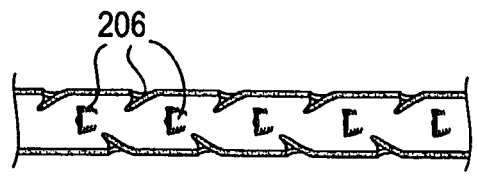
Figure 12C:
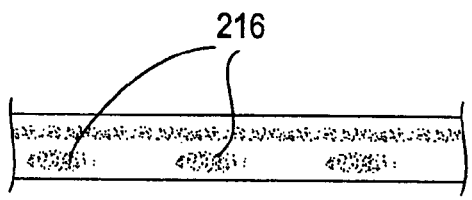
Figure 12D:
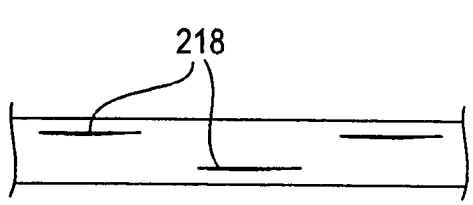
Figure 12E:
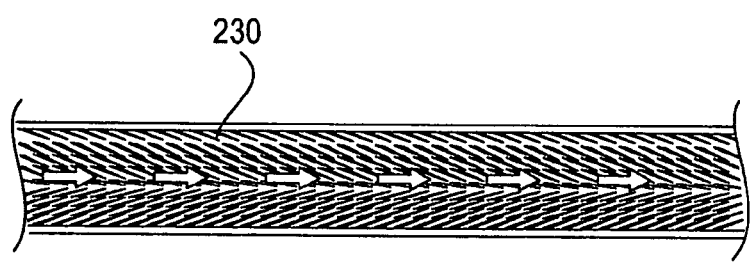

FIGS. 12A-12E are detail drawings showing additional features of a gastric or intestinal sleeve device. FIG. 12A shows a detail drawing of a gastric and/or intestinal sleeve device with openings 204 through the sleeve wall. Valves 206 may be provided in the wall of the gastric sleeve to allow digestive secretions to enter the sleeve, but to prevent solid food and/or nutrients from flowing out through the wall of the sleeve. FIG. 12B shows a detail drawing of a gastric and/or intestinal sleeve device with valved openings 206 through the sleeve wall. Alternatively, the entire gastric sleeve 200 or a portion of it can be nonporous or impermeable to act as an internal gastric bypass. FIG. 12C shows a detail drawing of a gastric and/or intestinal sleeve device with porous sections 216 in the wall of the sleeve. FIG. 12D shows a detail drawing of a gastric and/or intestinal sleeve device with slits 218 in the wall of the sleeve. FIG. 12E shows a detail drawing of a gastric or intestinal sleeve device with artificial cilia 230 on the interior of the sleeve wall. The artificial cilia 230 facilitate the flow of food through the sleeve. Alternatively or in addition, a hydrogel coating or other lubricious coating may be used to facilitate the flow of food through the sleeve.

The proximal (food entry) opening of the gastric sleeve is dimensioned to correspond to the opening of the pouch outlet or artificial stoma. These outlets are less than 10 mm in diameter and are typically 5 mm or less. This distal end of the sleeve is reinforced and/or configured for attachment to the surgical or artificial stoma opening. This opening is preferentially slightly larger than the diameter of the opening. Past the attachment to the opening the sleeve itself is preferentially 20-30 mm in diameter with a smooth transition from the opening diameter to the main diameter. If the sleeve continues past the pylorus, at the pylorus this diameter may reduce to a smaller diameter on the order of 10-20 mm. The sleeve should not be in sealing contact with the stomach wall or the pylorus to allow free passage of gastric secretions along the outside of the sleeve.

Figure 13:
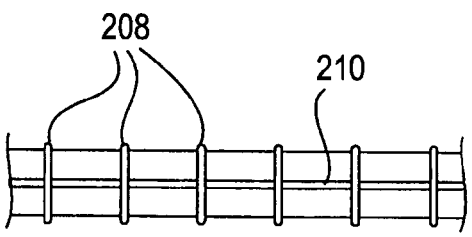
FIG. 13 shows a detail drawing of a gastric or intestinal sleeve device with reinforcement rings.
Figure 14:
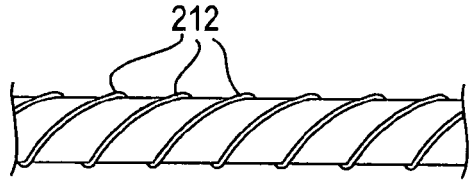
FIG. 14 shows a detail drawing of a gastric or intestinal sleeve device with a spiral reinforcement.

The wall of the gastric sleeve 200 is preferably flexible to allow the peristaltic motions of the stomach to effect movement of food through the gastric sleeve 200. Suitable materials for construction of the gastric sleeve device 200 include silicone and polyurethane. Silicone (e.g. Dow Silastic or similar material from Nusil) or polyurethane (e.g. Dow Pellethane) can be dip molded or cast. Polyurethane can also be blow molded. The wall of the sleeve may be reinforced with rings or a spiral made of wire and/or plastic to hold the sleeve open. FIG. 13 shows a detail drawing of a gastric and/or intestinal sleeve device with reinforcement rings 208. The reinforcement rings 208 are spaced apart at intervals along the length of the sleeve and the sleeve may include one or more longitudinal ribs 210 linking the reinforcement rings together along the length of the sleeve. FIG. 14 shows a detail drawing of a gastric and/or intestinal sleeve device with a spiral reinforcement 212. The reinforcement rings 208 or spiral reinforcement 212 should be resilient enough that peristaltic motions of the stomach and/or intestines can be transmitted through the wall of the sleeve with the sleeve springing back to its full diameter after the peristaltic contractions. The resiliency of the reinforcement rings 208 or spiral reinforcement 212 also allows the sleeve to be collapsed to facilitate endoscopic placement of the device. The reinforcement rings 208 or spiral reinforcement 212 may be made of stainless steel or a superelastic or shape-memory NiTi alloy. The reinforcement rings 208 or spiral reinforcement 212 can also be plastic. The reinforcement rings 208 or spiral reinforcement 212 may be sized to fit loosely within the stomach or intestines or to provide a little bit of contact force to create a seal with the intestinal walls. The interior and exterior of the sleeve can optionally be coated with a low friction material (e.g. a hydrogel) to reduce friction of food passage (interior) and reduce gastric irritation (exterior). The interior of the sleeve can optionally include flexible prongs angled toward the direction of food flow to act as artificial cilia and resist food moving retrograde along the sleeve, as shown in FIG. 12E.

In conjunction with the gastric sleeve 200, the volume of the stomach can be reduced by suturing, stapling or banding using open, transesophageal or laparoscopic techniques. In the exemplary application shown in FIG. 10, a vertical line of gastroplasty sutures or staples 104 parallel to the sleeve 200 has been used to reduce gastric volume. Alternatively or in addition, a horizontal line of gastroplasty sutures or staples may be used to form a reduced volume gastric pouch. The sutures or staples may or may not be in a continuous line and may or may not be reversible. These adjunctive techniques may assist in enhancing the effect of peristaltic motions of the stomach for moving food through the gastric sleeve.

Alternatively or in addition, a gastric balloon or other volume displacement device may be used in conjunction with the gastric sleeve to provide a feeling of satiety.

Preferably, the gastric sleeve is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted gastric sleeve can be verified noninvasively.

Figure 15:
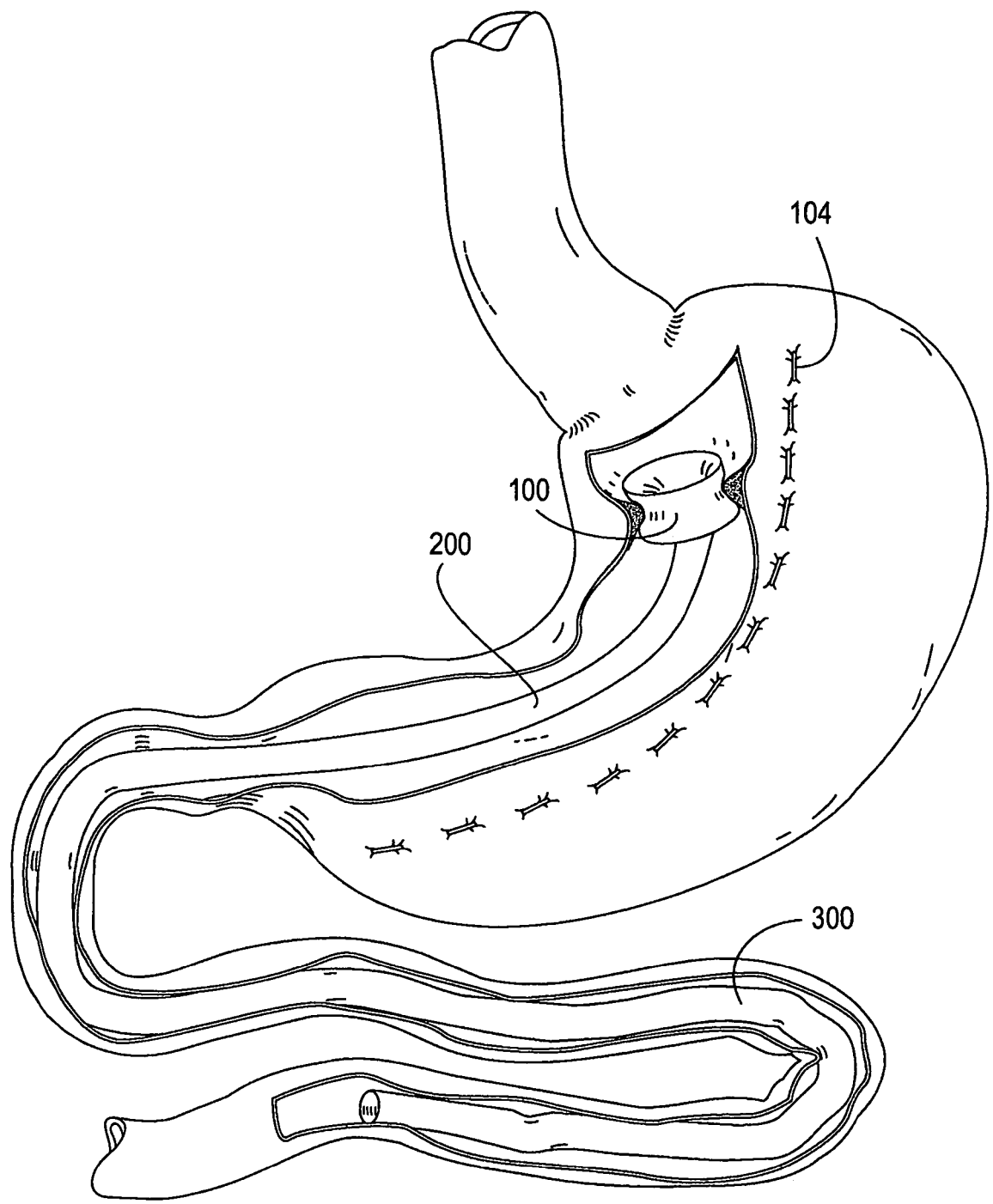
FIG. 15 shows a combined gastric and intestinal sleeve device with an artificial stoma device implanted within a patient's stomach with a line of gastroplasty sutures or staples parallel to the sleeve.
Figure 15A:
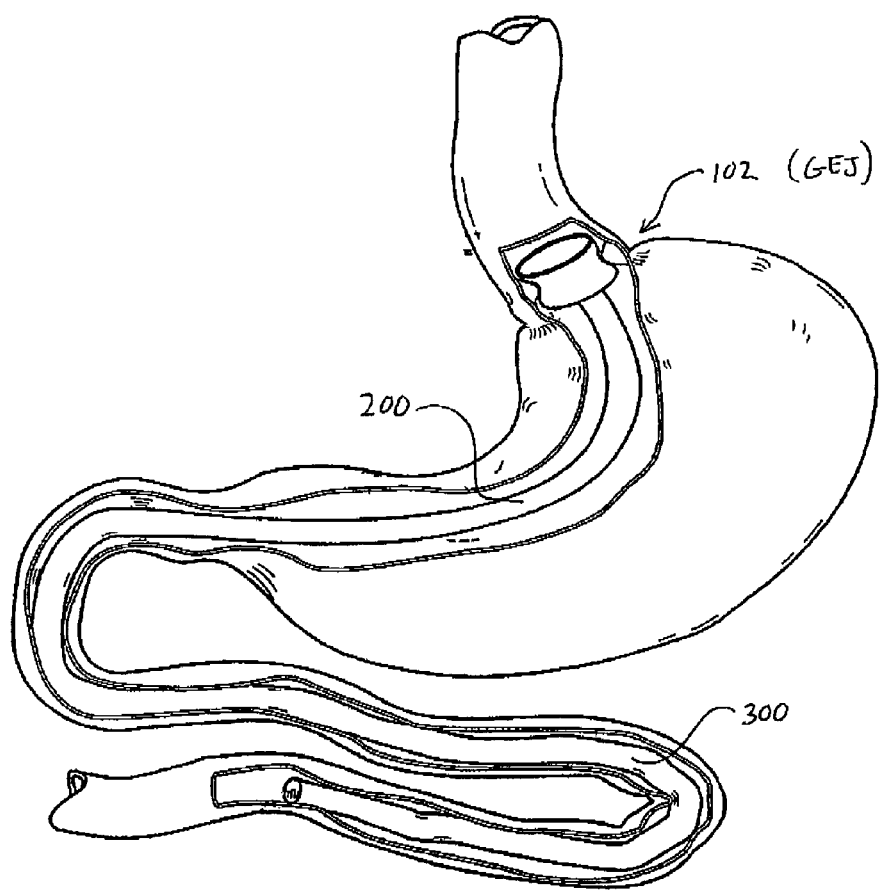
FIG. 15A shows a combined gastric and intestinal sleeve device attached at the gastroesophageal junction.

The third major component of the system is an internal intestinal sleeve 300 that may be used separately or used with, attached to or integrated with the internal gastric sleeve 200 and artificial stoma component 100. FIG. 15 shows a combined gastric 200 and intestinal 300 sleeve device with an artificial stoma device 100 implanted within a patient's stomach with a line of gastroplasty sutures or staples parallel to the sleeve 104. FIG. 15A shows a sleeve device having both gastric 200 and intestinal 300 sleeve portions implanted in the vicinity of the gastroesophageal junction 102, and without the line of gastroplasty sutures or staples. The entire intestinal sleeve 300 or a portion of it can be porous or semipermeable to allow the flow of digestive secretions into the sleeve and to allow the flow of nutrients and/or fluids out trough the wall of the sleeve. Suitable materials for construction of the intestinal sleeve device 300 include silicone (e.g. Dow Silastic or similar material from Nusil) and polyurethane (e.g. Pellethane). Openings 204 may be provided through the wall of the sleeve, as shown in FIG. 12A. Valves 206 maybe provided in the wall of the intestinal sleeve to allow digestive secretions to enter the sleeve, but to prevent solid food and/or nutrients from flowing out through the wall of the sleeve, as shown in FIG. 12B. Alternatively, the entire intestinal sleeve or a portion of it can be nonporous or impermeable to act as an internal intestinal bypass. The wall of the intestinal sleeve 300 is preferably flexible to allow the peristaltic motions of the intestinal wall to effect movement of food through the intestinal sleeve. The interior and exterior of the sleeve can optionally be coated with a low friction material (e.g. a hydrogel) to reduce friction of food passage (interior) and reduce intestinal irritation (exterior). The interior of the sleeve can optionally include flexible prongs angled toward the direction of food flow to act as artificial cilia and resist food moving retrograde along the sleeve, as shown in FIG. 12E. The wall of the sleeve may be reinforced with rings 208 or a spiral 212 made of wire and/or plastic, as shown in FIGS. 13 and 14. Optionaiiy the intestinal sleeve can include means for stabilization at the distal end such as a brush (as described by Berry), weight or inflatable balloon.

Dimensioning of the intestinal sleeve diameter is typically 15-30 mm with an optional smaller diameter at the point the sleeve passes through the pylorus (if the sleeve passes through the pylorus). The diameter of the sleeve is selected to be smaller that the diameter of the intestine. The sleeve should not be in sealing contact with the intestinal wall or the pylorus to allow free passage of gastric, billiary, pancreatic and intestinal secretions along the outside of the sleeve.

Figure 16:
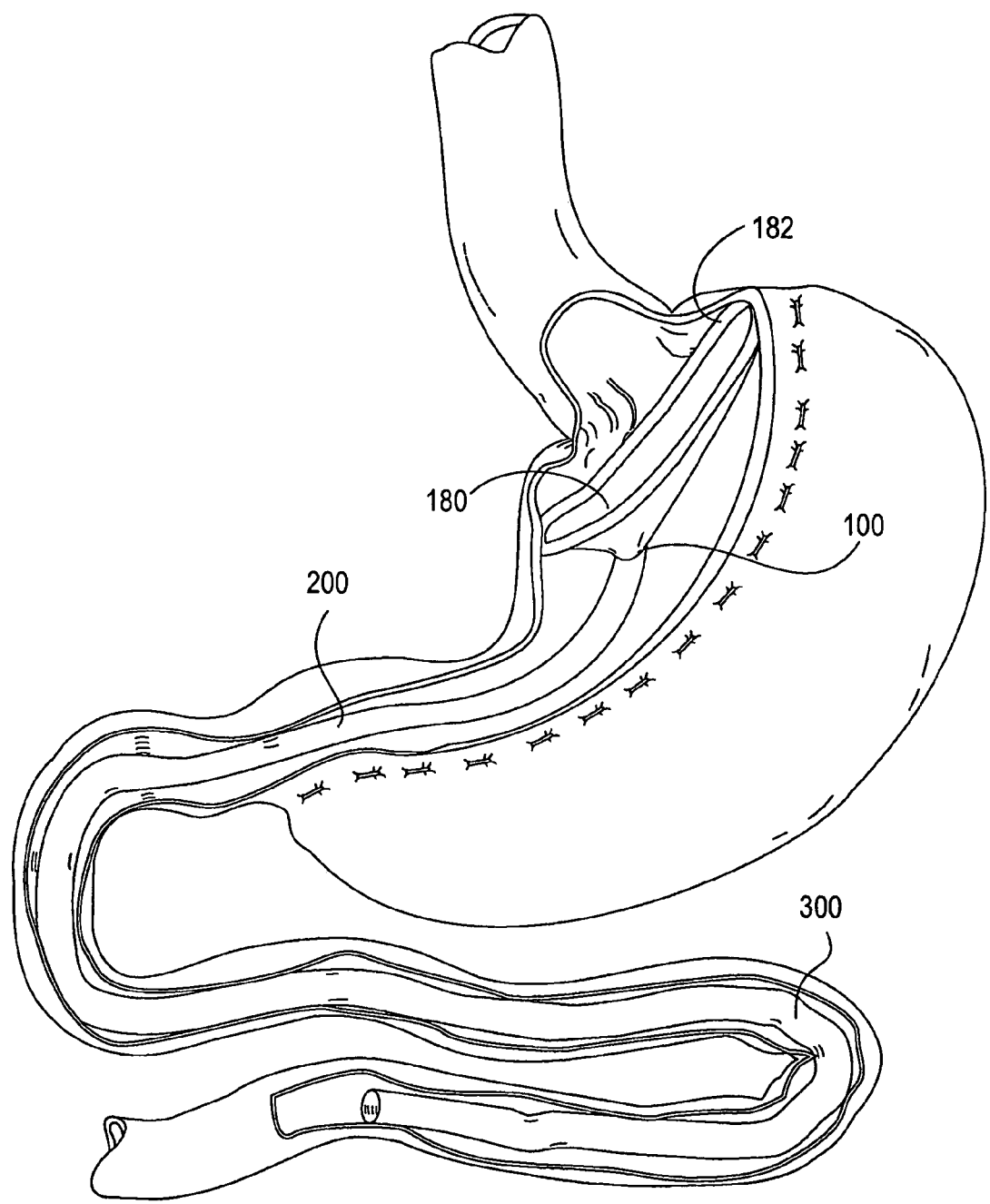
FIG. 16 shows a combined gastric and intestinal sleeve device with an artificial stoma device located within a funnel-shaped entry with a reinforced suture area.

Optionally, the intestinal sleeve 300 may have a proximal end with a reinforced anchoring segment or other anchoring mechanism for attachment in the region of the pylorus or the proximal end of the intestinal sleeve 300 may be attached to a stoma device or surgically created stoma at the outlet of a reduced stomach. Alternatively, the intestinal sleeve 300 may be attached to or continuous with the internal gastric sleeve 200. Optionally, the distal end of the intestinal sleeve 300 may include an anchoring mechanism. FIG. 16 shows a combined gastric 200 and intestinal 300 sleeve device with an artificial stoma device 100 located within a funnel-shaped entry 180 with a reinforced suture area 182. The funnel-shaped entry 180 creates a reduced-volume pouch within the patient's stomach that functions similarly to a surgically created gastroplasty pouch.

The intestinal sleeve 300 is preferably approximately 60-180 cm in length whereby partially digested or undigested nutrients exit from the sleeve into the jejunum where they can elicit a hormonal, neural and/or osmotic reaction in the jejunum and/or ileum. Increasing the length of the sleeve can increase the degree of response in the ileum.

The gastric sleeve 200 and/or intestinal sleeve 300 may be implanted according to the following method:

Sleeve Placement

At any point in the procedure for stoma implantation described above, preferably prior to suturing of the gastric pouch (step 8), a gastric and/or intestinal sleeve device may be placed in the stomach and/or intestines. The distal end of the intestinal sleeve is place endoscopically approximately 100 cm distal to the pylorus. The proximal end of the sleeve is attached, then the gastric pouch is sutured or stapled and the stoma placement procedure is resumed at step 9. Alternatively, the gastric and/or intestinal sleeve device may be placed after a pouch is formed and the stoma is placed, provided the stoma opening is sufficiently large to allow passage and manipulation of the sleeve and visualization apparatus. In the case of an intestinal sleeve, the proximal end would preferably be attached at the outlet of the stomach or at the pylorus. In the case of a gastric sleeve or combined gastric and intestinal sleeve, the proximal end would preferably be attached to a stoma device or surgically created stoma. Alternatively, the sleeve can be attached to the stomach or esophageal wall. In situations where it is desirable for the distal end of the sleeve to be placed further than 100 cm distal to the pylorus, the sleeve will be inserted in a collapsed configuration and restrained in the collapsed configuration by a bioabsorbable/dissolvable means and passed through the intestines by the normal peristaltic action of the intestine. This is similar to the use of peristaltic action for passage of a Baker tube as know in the art.

In an alternative method, the gastric and/or intestinal sleeve device may be used with a stoma device placed using standard surgical techniques, with a surgically created stoma, with surgical gastric banding or it may be used alone with no stoma device at all.

Preferably, the intestinal sleeve is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted intestinal sleeve can be verified noninvasively.

FIG. 17 shows an artificial stoma device 100 implanted within a patient's stomach with a line of gastroplasty sutures or staples 104 to reduce the gastric volume. Also shown is a line of sutures or staples 304 longitudinally dividing the small intestine to create a bile/pancreatic channel 308 separate from the intestinal lumen 310. The biliopancreatic channel 308 serves to prevent the patient's bile from mixing with the food in the intestinal lumen 310, thus reducing the digestion and absorption of fat.

FIG. 18 shows a cross section of the patient's small intestine showing the bile/pancreatic channel 308.

Figures 19, 20:
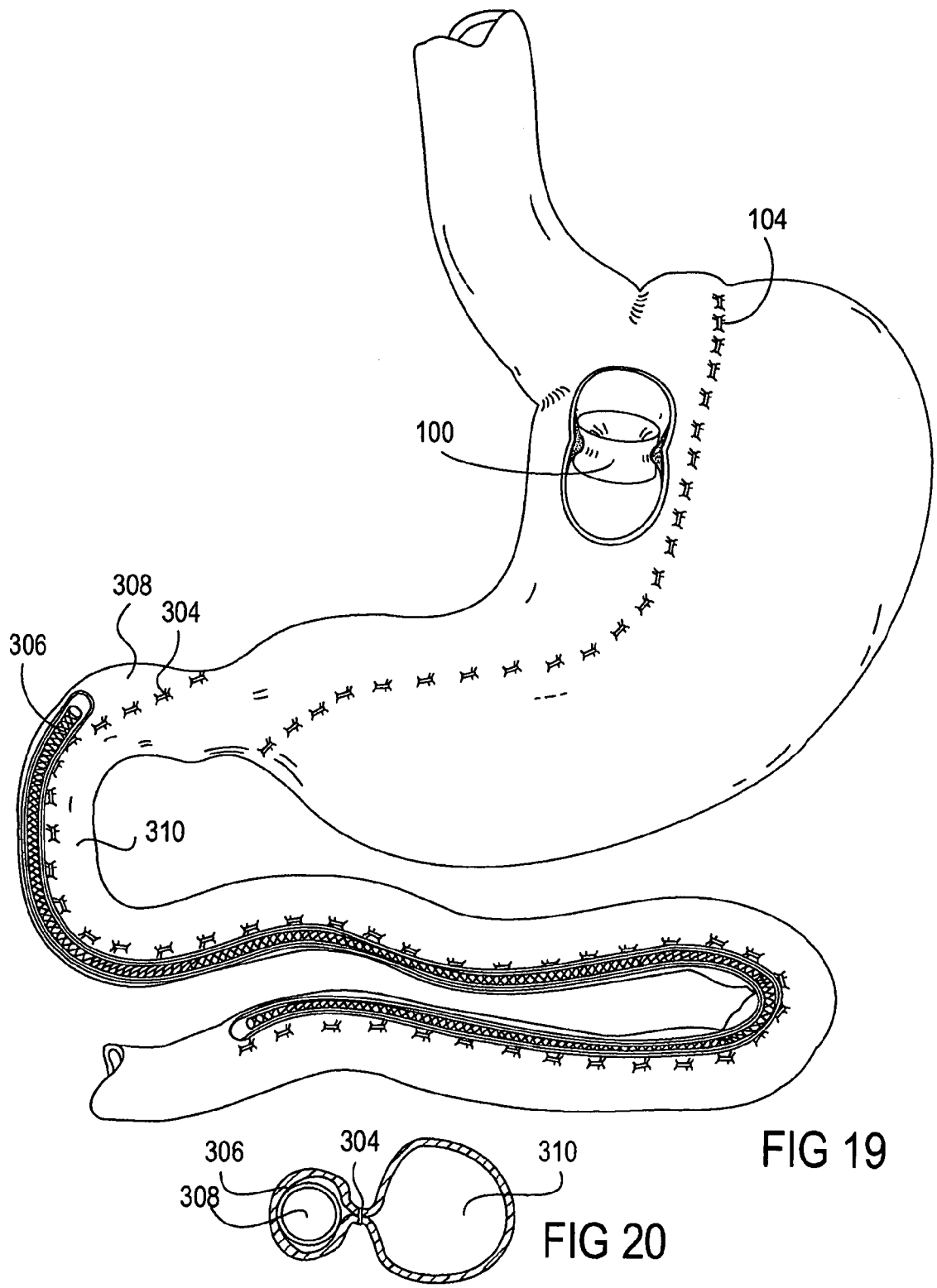
FIG. 19 shows an artificial stoma device implanted within a patient's stomach with a line of gastroplasty sutures or staples to reduce the gastric volume and a line of sutures or staples longitudinally dividing the small intestine to create a biliopancreatic channel with an optional stent.
FIG. 20 shows a cross section of the patient's small intestine showing the biliopancreatic channel with an optional stent.

FIG. 19 shows an artificial stoma device 100 implanted within a patient's stomach with a line of gastroplasty sutures or staples 104 to reduce the gastric volume and a line of sutures or staples 304 longitudinally dividing the small intestine to create a biliopancreatic channel 308 separate from the intestinal lumen 310 with an optional stent 306 to keep the bile/pancreatic channel 308 open and prevents collapse of the channel.

FIG. 20 shows a cross section of the patient's small intestine showing the biliopancreatic channel 308 with an optional stent 306.

Figure 21:
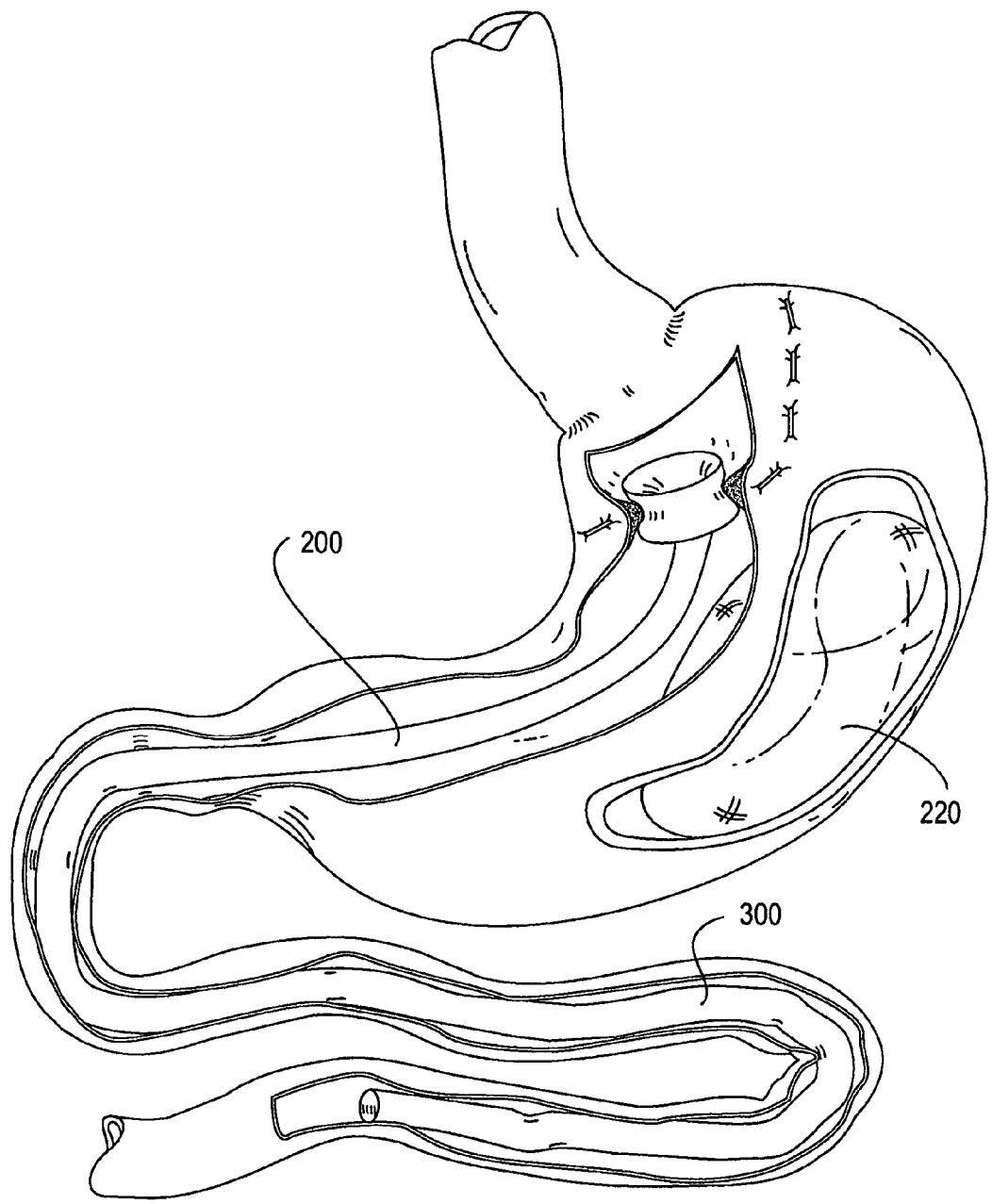
FIG. 21 shows a combined gastric and intestinal sleeve device implanted within a patient's stomach with a gastric balloon to reduce the gastric volume.

FIG. 21 shows a combined gastric 200 and intestinal 300 sleeve device implanted within a patient's stomach with a gastric balloon 220 to reduce the gastric volume.

In summary, the invention provides a method and system for treatment of morbid obesity that has three major components, an artificial stoma device, an internal gastric sleeve and an internal intestinal sleeve, which can be used separately or in combination. The artificial stoma device is implanted into a patient's stomach or lower esophagus to restrict food intake. The artificial stoma device may have a fixed aperture, an adjustable aperture or an aperture that varies in response to changing stomach conditions. The artificial stoma device may be implanted using sutures, staples, a reinforced anchoring segment or a sutureless attachment mechanism. The internal gastric sleeve may be separate from or integrated with the artificial stoma device. The internal gastric sleeve effectively reduces the patient's gastric volume and restricts the absorption of nutrients and calories from the food that passes through the stomach. The internal intestinal sleeve may be separate from or integrated with the internal gastric sleeve and/or the artificial stoma device. The wall of the internal gastric sleeve and/or internal intestinal sleeve may be constructed with reinforcing rings or a spiral reinforcement. The wall of the internal gastric sleeve and/or internal intestinal sleeve may have openings or valves to allow or restrict the digestive secretions and nutrients through the wall of the sleeve. Along with these major components, the treatment system may also include an attachment system that uses wire fasteners for performing a gastrostomy and a stent for supporting a bile/pancreatic channel in the patient's small intestine.

The method provided by this invention has the capacity to combine these various components into a system that treats obesity by creating a pouch with an outlet restriction which can be optionally controlled or operable, placing means by which the food exiting the pouch is transferred via gastric and intestinal sleeves to a point in the intestine while being substantially isolated from (or allowed to contact a controlled amount) gastric, biliary, pancreatic and intestinal secretions, whereby this location in the intestine can be optionally selected to induce various reactions of the intestinal tissue which may include dumping, hormonal secretion and/or nervous stimulation.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of treating a patient, comprising the steps of:
   providing an artificial stoma device;
   transesophageally advancing the device to an attachment site in the vicinity of the gastroesophageal junction; and
   attaching the device at the attachment site;
   wherein the attaching step comprises advancing at least one anchor through a delivery cannula and through the wall of the stomach, the wall having a mucosal surface and a serosal surface, and positioning the anchor against the serosal surface; and
   wherein the anchor is enlargeable from a first configuration for passing through the cannula, to a second configuration for functioning as an anchor.

2. A method of treating a patient as in claim 1, further comprising the step of attaching a proximal end of an elongate flexible tube to the stoma device, and positioning a distal end of the elongate tube in the intestine.

3. A method of treating a patient as in claim 1, wherein the stoma device provides a stoma having an inside diameter approximately equal to the diameter of the gastroesophageal junction.

4. A method of treating a patient as in claim 1, wherein the anchor is biased toward the second configuration.

5. A method of treating a patient as in claim 4, wherein the second configuration comprises a button shape.

6. A method of treating a patient, comprising the steps of:
   providing an elongate tubular sleeve having a proximal end and a distal end;
   transesophageally advancing the sleeve to an attachment site in the vicinity of the gastroesophageal junction;
   positioning the distal end of the sleeve in the intestine; and
   attaching the proximal end of the sleeve at the attachment site;
   wherein the attaching step comprises advancing at least one anchor through the wall of the stomach, the wall having a mucosal surface and a serosal surface, and positioning the anchor against the serosal surface.

7. A method of treating a patient as in claim 6, wherein the advancing step comprises advancing the anchor through a delivery cannula.

8. A method of treating a patient as in claim 7, wherein the anchor is enlargeable from a first configuration for passing through the cannula, to a second configuration for functioning as an anchor.

9. A method of treating a patient as in claim 8, wherein the anchor is biased toward the second configuration.

10. A method of treating a patient as in claim 9, wherein the second configuration comprises a button shape.

11. A method of treating a patient as in claim 6, wherein at least a portion of the sleeve has a diameter of 20 to 30 mm.

12. A method of treating a patient as in claim 6, wherein at least a portion of the sleeve has a diameter on the order of 10 to 20 mm.

13. A method of treating a patient as in claim 6, wherein the wall of the sleeve is sufficiently flexible to allow peristaltic motion of the stomach to move food through the sleeve.

14. A method of treating a patient as in claim 6, wherein the providing step comprises providing an elongate tubular sleeve having reinforcement rings.

15. A method of treating a patient as in claim 6, wherein the providing step comprises providing an elongate tubular sleeve having a low friction coating.

16. A method of treating a patient as in claim 6, additionally comprising the step of reducing the volume of the stomach.

17. A method of treating a patient as in claim 6, wherein the providing step comprises providing an elongate tubular sleeve having one or more radiopaque marker.

18. A method of treating a patient as in claim 6, wherein at least a portion of the sleeve is semi-permeable.

19. A method of treating a patient as in claim 6, wherein at least a portion of the sleeve is impermeable.

20. A method of treating a patient as in claim 6, wherein the positioning the distal end of the sleeve step comprising positioning the distal end of the sleeve such that partially digested or undigested nutrients exit from the sleeve into the jejunum.

21. A method of treating a patient as in claim 6, wherein the providing step comprises providing an elongate tubular sleeve having a length of approximately 60 to 180 cm.

22. A method of treating a patient, comprising the steps of:
providing an elongate tubular sleeve having a proximal end and a distal end, wherein at least a portion of the sleeve is semi-permeable;
transesophageally advancing the sleeve to an attachment site in the vicinity of the gastroesophageal junction; and
attaching the proximal end of the sleeve at the attachment site;
wherein the attaching step comprises advancing at least one anchor through the wall of the stomach, the wall having a mucosal surface and a serosal surface, and positioning the anchor against the serosal surface.

23. A method of treating a patient as in claim 22, further comprising the step of positioning the distal end of the sleeve in the intestine.

24. A method of treating a patient as in claim 23, wherein the positioning the distal end of the sleeve step comprising positioning the distal end of the sleeve such that partially digested or undigested nutrients exit from the sleeve into the jejunum.

25. A method of treating a patient as in claim 22, wherein the advancing step comprises advancing the anchor through a delivery cannula.

26. A method of treating a patient as in claim 25, wherein the anchor is enlargeable from a first configuration for passing through the cannula, to a second configuration for functioning as an anchor.

27. A method of treating a patient as in claim 26, wherein the anchor is biased toward the second configuration.

28. A method of treating a patient as in claim 27, wherein the second configuration comprises a button shape.

29. A method of treating a patient as in claim 22, wherein at least a portion of the sleeve has a diameter of 20 to 30 mm.

30. A method of treating a patient as in claim 22, wherein at least a portion of the sleeve has a diameter on the order of 10 to 20 mm.

31. A method of treating a patient as in claim 22, wherein the wall of the sleeve is sufficiently flexible to allow peristaltic motion of the stomach to move food through the sleeve.

32. A method of treating a patient as in claim 22, wherein the providing step comprises providing an elongate tubular sleeve having reinforcement rings.

33. A method of treating a patient as in claim 22, wherein the providing step comprises providing an elongate tubular sleeve having a low friction coating.

34. A method of treating a patient as in claim 22, additionally comprising the step of reducing the volume of the stomach.

35. A method of treating a patient as in claim 22, wherein the providing step comprises providing an elongate tubular sleeve having one or more radiopaque marker.

36. A method of treating a patient as in claim 22, wherein at least a portion of the sleeve is impermeable.

37. A method of treating a patient as in claim 22, wherein the providing step comprises providing an elongate tubular sleeve having a length of approximately 60 to 180 cm.

38. A method of treating a patient, comprising the steps of:
providing an elongate tubular sleeve having a proximal end and a distal end, wherein at least a portion of the sleeve is semi-permeable;
transesophageally advancing the sleeve to an attachment site in the vicinity of the gastroesophageal junction;
attaching the proximal end of the sleeve at the attachment site; and
positioning the distal end of the sleeve in the intestine, wherein the positioning the distal end of the sleeve step comprising positioning the distal end of the sleeve such that partially digested or undigested nutrients exit from the sleeve into the jejunum;
wherein the attaching step comprises advancing at least one anchor through the wall of the stomach, the wall having a mucosal surface and a serosal surface, and positioning the anchor against the serosal surface.

39. A method of treating a patient as in claim 38, wherein the advancing step comprises advancing the anchor through a delivery cannula.

40. A method of treating a patient as in claim 39, wherein the anchor is enlargeable from a first configuration for passing through the cannula, to a second configuration for functioning as an anchor.

41. A method of treating a patient as in claim 40, wherein the anchor is biased toward the second configuration.

42. A method of treating a patient as in claim 41, wherein the second configuration comprises a button shape.

43. A method of treating a patient as in claim 38, wherein at least a portion of the sleeve has a diameter of 20 to 30 mm.

44. A method of treating a patient as in claim 38, wherein at least a portion of the sleeve has a diameter on the order of 10 to 20 mm.

45. A method of treating a patient as in claim 38, wherein the wall of the sleeve is sufficiently flexible to allow peristaltic motion of the stomach to move food through the sleeve.

46. A method of treating a patient as in claim 38, wherein the providing step comprises providing an elongate tubular sleeve having reinforcement rings.

47. A method of treating a patient as in claim 38, wherein the providing step comprises providing an elongate tubular sleeve having a low friction coating.

48. A method of treating a patient as in claim 38, additionally comprising the step of reducing the volume of the stomach.

49. A method of treating a patient as in claim 38, wherein the providing step comprises providing an elongate tubular sleeve having one or more radiopaque marker.

50. A method of treating a patient as in claim 38, wherein at least a portion of the sleeve is semi-permeable.

51. A method of treating a patient as in claim 38, wherein at least a portion of the sleeve is impermeable.

52. A method of treating a patient as in claim 38, wherein the providing step comprises providing an elongate tubular sleeve having a length of approximately 60 to 180 cm.

53. A method of treating a patient, comprising the steps of:
providing an elongate tubular sleeve having a proximal end and a distal end;
transesophageally advancing the sleeve to an attachment site in the vicinity of the gastroesophageal junction; and
attaching the proximal end of the sleeve at the attachment site;
wherein the attaching step comprises advancing at least one anchor through a delivery cannula, and through the wall of the stomach, the wall having a mucosal surface and a serosal surface, and positioning the anchor against the serosal surface;
wherein the anchor is enlargeable from a first configuration for passing through the cannula, to a second configuration for functioning as an anchor.

54. A method of treating a patient as in claim 53, further comprising the step of positioning the distal end of the sleeve in the intestine.

55. A method of treating a patient as in claim 54, wherein the positioning the distal end of the sleeve step comprising positioning the distal end of the sleeve such that partially digested or undigested nutrients exit from the sleeve into the jejunum.

56. A method of treating a patient as in claim 53, wherein the anchor is biased toward the second configuration.

57. A method of treating a patient as in claim 56, wherein the second configuration comprises a button shape.

58. A method of treating a patient as in claim 53, wherein at least a portion of the sleeve has a diameter of 20 to 30 mm.

59. A method of treating a patient as in claim 53, wherein at least a portion of the sleeve has a diameter on the order of 10 to 20 mm.

60. A method of treating a patient as in claim 53, wherein the wall of the sleeve is sufficiently flexible to allow peristaltic motion of the stomach to move food through the sleeve.

61. A method of treating a patient as in claim 53, wherein the providing step comprises providing an elongate tubular sleeve having reinforcement rings.

62. A method of treating a patient as in claim 53, wherein the providing step comprises providing an elongate tubular sleeve having a low friction coating.

63. A method of treating a patient as in claim 53, additionally comprising the step of reducing the volume of the stomach.

64. A method of treating a patient as in claim 53, wherein the providing step comprises providing an elongate tubular sleeve having one or more radiopaque marker.

65. A method of treating a patient as in claim 53, wherein at least a portion of the sleeve is semi-permeable.

66. A method of treating a patient as in claim 53, wherein at least a portion of the sleeve is impermeable.

67. A method of treating a patient as in claim 53, wherein the providing step comprises providing an elongate tubular sleeve having a length of approximately 60 to 180 cm.

* * * * *

UNITED STATES PATENT AND TRADEMARK OFFICE
CERTIFICATE OF CORRECTION

PATENT NO. : 7,220,284 B2
APPLICATION NO. : 11/169341
DATED : May 22, 2007
INVENTOR(S) : Kagan et al.

It is certified that error appears in the above-identified patent and that said Letters Patent is hereby corrected as shown below:

Title Page; item (60);

In Col. 1, line 1, Delete "60/442,987," and insert -- 60/422,987, --, therefor.

In Col. 1, line 12, Delete "60/442,987," and insert -- 60/422,987, --, therefor.

In Col. 19, line 63, Delete "trough" and insert -- through --, therefor.

In Col. 20, line 1, Delete "maybe" and insert -- may be --, therefor.

In Col. 20, line 19, Delete "Optionaiiy" and insert -- Optionally --, therefor.

In Col. 20, line 59, Delete "place" and insert -- placed --, therefor.

Signed and Sealed this

Sixth Day of November, 2007

JON W. DUDAS
*Director of the United States Patent and Trademark Office*